US010882892B2

(12) United States Patent
Klapoetke et al.

(10) Patent No.: US 10,882,892 B2
(45) Date of Patent: Jan. 5, 2021

(54) CHANNELRHODOPSIN VARIANTS AND USES THEREOF

(71) Applicants: Massachusetts Institute of Technology, Cambridge, MA (US); The Governors of the University of Alberta, Edmonton, Alberta (CA)

(72) Inventors: Nathan Klapoetke, Ashburn, VA (US); Brian Yichiun Chow, Cherry Hill, NJ (US); Edward Boyden, Chestnut Hill, MA (US); Gane Ka-Shu Wong, Edmonton (CA); Yongku Peter Cho, Vernon, CT (US)

(73) Assignees: Massachusetts Institute of Technology, Cambridge, MA (US); The Governors of The University of Alberta, Edmonton (CA)

( * ) Notice: Subject to any disclaimer, the term of this patent is extended or adjusted under 35 U.S.C. 154(b) by 111 days.

(21) Appl. No.: 14/817,335

(22) Filed: Aug. 4, 2015

(65) Prior Publication Data
US 2016/0039902 A1 Feb. 11, 2016

Related U.S. Application Data

(60) Provisional application No. 62/033,213, filed on Aug. 5, 2014.

(51) Int. Cl.
| | |
|---|---|
| *A61K 38/00* | (2006.01) |
| *A61K 38/16* | (2006.01) |
| *A61P 9/10* | (2006.01) |
| *A61P 27/02* | (2006.01) |
| *C07K 14/705* | (2006.01) |
| *A61K 41/00* | (2020.01) |
| *A61N 5/06* | (2006.01) |
| *C07K 14/435* | (2006.01) |
| *G01N 33/68* | (2006.01) |

(52) U.S. Cl.
CPC ........... *C07K 14/705* (2013.01); *A61K 38/16* (2013.01); *A61K 41/00* (2013.01); *A61N 5/0613* (2013.01); *C07K 14/43581* (2013.01); *G01N 33/6872* (2013.01); *A61K 38/00* (2013.01); *A61N 5/062* (2013.01); *G01N 2333/705* (2013.01)

(58) Field of Classification Search
None
See application file for complete search history.

(56) References Cited

U.S. PATENT DOCUMENTS

| | | |
|---|---|---|
| 5,041,224 A | 8/1991 | Ohyama et al. |
| 6,197,387 B1 | 3/2001 | Feidler et al. |
| 7,824,869 B2 | 11/2010 | Hegemann et al. |
| 7,939,220 B2 | 5/2011 | Oesterhelt et al. |
| 8,202,699 B2 | 6/2012 | Hegemann et al. |
| 8,401,609 B2 | 3/2013 | Deisseroth et al. |
| 2007/0053996 A1 | 3/2007 | Boyden et al. |
| 2007/0054319 A1 | 3/2007 | Boyden et al. |
| 2007/0261127 A1 | 11/2007 | Boyden et al. |
| 2009/0099038 A1 | 4/2009 | Deisseroth et al. |
| 2010/0087006 A1 | 4/2010 | Gressel et al. |
| 2010/0145418 A1 | 6/2010 | Zhang et al. |
| 2010/0234273 A1 | 9/2010 | Boyden et al. |
| 2011/0165681 A1 | 7/2011 | Boyden et al. |
| 2012/0121542 A1 | 5/2012 | Chuong et al. |
| 2012/0214188 A1 | 8/2012 | Klapoetke et al. |
| 2014/0324134 A1 | 10/2014 | Klapoetke et al. |
| 2015/0192567 A1 | 7/2015 | Chuong et al. |
| 2017/0088590 A1 | 3/2017 | Klapoetke et al. |

FOREIGN PATENT DOCUMENTS

| | | |
|---|---|---|
| EP | 2112510 A1 | 10/2009 |
| WO | 2007024391 A3 | 3/2007 |
| WO | 2009119782 A1 | 10/2009 |
| WO | 2010056970 A2 | 5/2010 |
| WO | 2012061676 A1 | 5/2012 |
| WO | 2012061744 A2 | 5/2012 |
| WO | 2013071231 A1 | 5/2013 |

OTHER PUBLICATIONS

Haltiwanger, S., "The Electrical Properties of Cancer Cells," available online at http://www.royalrife.com/haltiwanger1.pdf, 62 pages, (1st available 2003).*
Kishmore, P., "Diabetes Mellitus (DM)", Merck Manual, available online at https://www.merckmanuals.com/professional/endocrine-and-metabolic-disorders/diabetes-mellitus-and-disorders-of-carbohydrate-metabolism/diabetes-mellitus-dm, 38 pages (Jun. 2014).*
Klapoetke et al., Nature Methods 11:338-346 (first available Feb. 9, 2014) with Corrigendum, Addendum, and Supplemental Figures (first available Aug. 28, 2014).*
Bowie et al. (Science, 1990, 247:1306-1310).*
Burgess et al. (J. Cell Biol. 111:2129-2138, 1990).*
Bork (Genome Research, 2000, 10:398-400).*
(Chang, B.S. and Hershenson, S. 2002. Practical approaches to protein formulation development in "Rationale Design of stable protein formulations-theory and practice" (J.F. Carpenter and M.C. Manning eds.) Kluwer Academic/Plenum publishers, New York. pp. 1-25.).*
Lazar et al. (Mol. Cell. Biol., 8:1247-1252, 1988).*
Inaguma et al., J. Biol. Chem. 290:11623-11634 (2015).*
Lin, Exp. Physiol. 96:19-25 (2010).*
Yawo et al., Develop. Growth Diff. pp. 1-17 (2013).*

(Continued)

*Primary Examiner* — James H Alstrum-Acevedo
*Assistant Examiner* — Thea D'Ambrosio
(74) *Attorney, Agent, or Firm* — Pierce Atwood LLP

(57) ABSTRACT

CsChrimson light-activated ion channel polypeptides, their encoding polynucleotides, and variants thereof are provided. Methods of introducing and using CsChrimson light activated ion channels and variants thereof for to alter cell activity and function are also provided.

28 Claims, 5 Drawing Sheets
Specification includes a Sequence Listing.

(56) References Cited

OTHER PUBLICATIONS

Baliga, N.S. et al., "Genome sequence of Haloarcula marismortui: A halophilic archaeon from the Dead Sea", Genome Research, 2004, vol. 14, pp. 2221-2234.*.
Boyden, E. et al, "Millisecond-timescale, genetically targeted optical control of neural activity", Nature Neuroscience, Sep. 2005, vol. 8, pp. 1263-1268.
Busskamp, V. et al., "Genetic Reactivation of Cone Photoreceptors Restores Visual Responses in Retinitis Pigmentosa", Science, Jul. 23, 2010, vol. 329, pp. 413-417.
Chow, B. et al., "High-performance genetically targetable optical neural silencing by light-driven proton pumps", Nature, Jan. 7, 2010, vol. 463, pp. 98-102.
Chow, B. et al., "Synthetic Physiology Strategies for Adapting Tools from Nature for Genetically Targeted Control of Fast Biological Processes", Methods in Enzymology, 2011, vol. 497, pp. 425-443.
Chuong, A. et al., "Development of next-generation optical neural silencers through directed combinatorial optimization", Neuroscience 2010 Annual Meeting, Nov. 13, 2010, Presentation Abstract, 2 pages.
Chuong, A. et al., "Red-shifted optical neuronal silencing: optical hemoglobin transparency for long-distance optogenetic inhibition", Neuroscience 2010 Annual Meeting, Nov. 13, 2010, Poster Presentation, 1 page.
Dittgen, T. et al., "Lentivirus-based genetic manipulations of cortical neurons and their optical and electrophysiological monitoring in vivo", PNAS, Dec. 28, 2004, vol. 101, pp. 18206-18211.
Doroudchi, M. et al., "Virally delivered Channelrhodopsin-2 Safely and Effectively Restores Visual Function in Multiple Mouse Models of Blindness", Molecular Therapy, Jul. 2011, vol. 19, pp. 1220-1229.
Gradinaru, V. et al., "eNpHR: a Natronomonas halorhodopsin enhanced for optogenetic applications", Brain Cell Biology, 2008, vol. 36, pp. 129-139.
Gradinaru, V. et al., "Molecular and Cellular Approaches for Diversifying and Extending Optogenetics", Cell, Apr. 2, 2010, vol. 141, pp. 154-165.
Hackett, N. et al., "Structure-Function Studies on Bacteriorhodopsin", The Journal of Biological Chemistry, Jul. 5, 1987, vol. 262, pp. 9277-9284.
Han, X. & E. Boyden, "Multiple-Color Optical Activation, Silencing, and Desynchronization of Neural Activity, with Single-Spike Temporal Resolution", PloS one, Mar. 2007, Issue 3, pp. 1-12.
Han, X. et al., "A high-light sensitivity optical neural silencer: development and application to optogenetic control of non-human primate cortex", Frontiers in Systems Neuroscience, Apr. 13, 2011, vol. 5, pp. 1-8.
Han, X. et al., "Informational lesions: optical perturbation of spike timing and neural synchrony via microbial opsin gene fusions", Frontiers in Molecular Neuroscience, Aug. 27, 2009, vol. 2, pp. 1-9.
Ihara, K. et al., "Haloarcula argentinensis sp. nov. And Haloarcula mukohataei sp. nov., Two. New Extremely Halophilic Archaea Collected in Argentina", International Journal of Systematic Bacteriology, Jan. 1997, vol. 47, pp. 73-77.
Ihara, K. et al., "Evolution of the Archaeal Rhodopsins: Evolution Rate Changes by Gene Duplication and Functional Differentiation", Journal of Molecular Biology, 1999, vol. 285, pp. 163-174.
Javor, B et al., "Box-Shaped Halophilic Bacteria", Journal of Bacteriology, Sep. 1982, vol. 151, pp. 1532-1542.
Klare, J. et al., "Microbial Rhodopsins: Scaffolds for Ion Pumps, Channels, and Sensors", Results and Problems in Cell Differentiation Journal Impact Factor & Information, Sep. 27, 2007, vol. 45, pp. 73-122.
Kitajima, T. et al. "Novel Bacterial Rhodopsins from Haloarcula vallismortis", Biochemical and Biophysical Research Communications, 1996, vol. 220, pp. 341-345.

Kleinlogel, S. et al., "Ultra-light sensitive and fast neuronal activation with the Ca(2+)-permeable channelrhodopsin CatCh", Nature Neuroscience, Apr. 2011, vol. 14, pp. 513-518.
Lin, J. et al., "Characterization of Engineered Channelrhodopsin Variants with Improved Properties and Kinetics", Biophysical Journal, Mar. 4, 2009, vol. 96, pp. 1803-1814.
Mogi, T. et al, "Structure-Function Studies on Bacteriorhodopsin", The Journal of Biological Chemistry, Aug. 25, 1989, vol. 264, pp. 14197-14201.
Nagel, G. et al., "Channelrhodopsin-1: A Light-Gated Proton Channel in Green Algae", Science, Jun. 28, 2002, vol. 296, pp. 2395-2398.
Nagel, G. et al., "Channelrhodopsin-2, a directly light-gated cation-selective membrane channel", PNAS, Nov. 25, 2003, vol. 100, pp. 13940-13945.
Otomo, J., "Anion selectivity and pumping mechanism of halorhodopsin", Biophysical Chemistry, 1995, vol. 56, pp. 137-141.
Otomo, J. et al. "Bacterial rhodopsins of newly isolated halobacteria", Journal of General Microbiology, Jan. 6, 1992, vol. 138, pp. 1027-1037.
Otomo, J. & T. Muramatsu, "Over-expression of a new photo-active halorhodopsin in Halobacterium salinarium", Biochimica et Biophysica Acta, Aug. 1995, vol. 1240, pp. 248-256.
Rudiger, M. & D. Oesterhelt, "Specific arginine and threonine residues control anion binding and transport in the light-driven chloride pumo halorhodopsin", The EMBO Journal, 1997, vol. 16, pp. 3813-3821.
Tang et al., "Faithful Expression of Multiple Proteins via 2A-Peptide Self-Processing: A Versatile and Reliable Method for Manipulating Brain Circuits", The Journal of Neuroscience, Jul. 8, 2009, vol. 29, pp. 8621-8629.
Wang, H. et al., "High-speed mapping of synaptic connectivity using photostimulation in Channelrhodopsin-2 transgenic mice", PNAS, May 8, 2007, vol. 104, pp. 8143-8148. Epub May 1, 2007.
Yizhar, O. et al., "Neocortical excitation/inhibition balance in information processing and social dysfunction", Nature, Sep. 8, 2011, vol. 477, pp. 1-8.
Zhang, F. et al., "Multimodal fast optical interrogation of neural circuitry" Nature, 2007, pp. 633-639, vol. 446.
Zhang, F. et al., "Red-shifted optogenetic excitation: a tool for fast neural control derived from Volvox carteri", Nature Neuroscience, 2008, vol. 11, pp. 631-633.
Feldbauera, K. et al., "Channelrhodopsin-2 is a leaky proton pump", PNAS, Jul. 28, 2009, vol. 106, pp. 12317-12322.
Mukohata, Y. et al., "Halobacteria) Rhodopsins", Journal of Biochemistry, 1999, vol. 125, pp. 649-657.
International Search Report International Patent Application No. PCT/US2012/064665, dated Apr. 4, 2013, 5 pages.
International Preliminary Report on Patentability and Written Opinion of the International Searching Authority dated May 22, 2014 for International Patent Application No. PCT/US2012/064665, 9 pages.
Radu, I., et al., "Conformational changes of channelrhodopsin-2", J Am Chem Soc., Jun. 3, 2009, vol. 131, 1 page. Abstract only.
Nack, M., "The DC gate in Channelrhodopsin-2: crucial hydrogen bonding interaction between C128 and D156", Photochem Photobiol Sci., Feb. 2010, vol. 9, 1 page. Abstract only.
Sugiyama, Y., et al., "Photocurrent attenuation by a single polar-to-nonpolar point mutation of channelrhodopsin-2", Photochem Photobiol Sci., Mar. 2009, vol. 8, 1 page. Abstract only.
Krause et al. "Structural differences between the closed and open states of channelrhodopsin-2 observed by EPR spectroscopy." FEBS Letters 587 (2013) 3309-3313.
Lorenz-Fonfria et al. "Channelrhodopsin unchained: Structure and mechanism of a light-gated cation channel." BBA Biochimica et Biophysica Acta 1837 (2014) 626-642.
Klapoetke N. et al. "Independent optical excitation of distinct neural populations." Nature Methods (2014) 11:338-346 (first available Feb. 9, 2014) with corrigendum, Addendum, and Supplemental figures (first available Aug. 28, 2014), total pp. 79.

* cited by examiner trafficking version used for Drosophila transgenic

Kir2.1 KGC sequence: KSRITSEGEYIPLDQIDINV
Kir2.1 ER2 sequence: FCYENEV

Chrimson-GFP

CsChrimson-GFP

CsChrimson-KGC-GFP

CsChrimson-GFP-ER2

CsChrimson-KGC-GFP-ER2

SEQUENCE LISTING

```
<160> NUMBER OF SEQ ID NOS: 17

<210> SEQ ID NO 1
<211> LENGTH: 345
<212> TYPE: PRT
<213> ORGANISM: Artificial Sequence
<220> FEATURE:
<223> OTHER INFORMATION: Synthetic polypeptide

<400> SEQUENCE: 1

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Ala Val Ser His Tyr Ala Met Asn Gly
        35                  40                  45
```

```
Phe Asp Glu Leu Ala Lys Gly Ala Val Val Pro Glu Asp His Phe Val
 50                  55                  60

Cys Gly Pro Ala Asp Lys Cys Tyr Cys Ser Ala Trp Leu His Ser Arg
 65                  70                  75                  80

Gly Thr Pro Gly Glu Lys Ile Gly Ala Gln Val Cys Gln Trp Ile Ala
                 85                  90                  95

Phe Ser Ile Ala Ile Ala Leu Leu Thr Phe Tyr Gly Phe Ser Ala Trp
             100                 105                 110

Lys Ala Thr Cys Gly Trp Glu Glu Val Tyr Val Cys Cys Val Glu Val
             115                 120                 125

Leu Phe Val Thr Leu Glu Ile Phe Lys Glu Phe Ser Ser Pro Ala Thr
130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Lys Leu Ser Asn Leu Ser
                165                 170                 175

Gly Leu Lys Asn Asp Tyr Ser Lys Arg Thr Met Gly Leu Ile Val Ser
            180                 185                 190

Cys Val Gly Met Ile Val Phe Gly Met Ala Ala Gly Leu Ala Thr Asp
            195                 200                 205

Trp Leu Lys Trp Leu Leu Tyr Ile Val Ser Cys Ile Tyr Gly Gly Tyr
210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
            275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Glu Val Glu Val Glu Glu Phe
                325                 330                 335

Val Glu Glu Glu Asp Glu Asp Thr Val
            340                 345

<210> SEQ ID NO 2
<211> LENGTH: 350
<212> TYPE: PRT
<213> ORGANISM: Chlamydomonas noctigama

<400> SEQUENCE: 2

Met Ala Glu Leu Ile Ser Ser Ala Thr Arg Ser Leu Phe Ala Ala Gly
 1               5                  10                  15

Gly Ile Asn Pro Trp Pro Asn Pro Tyr His His Glu Asp Met Gly Cys
                 20                  25                  30

Gly Gly Met Thr Pro Thr Gly Glu Cys Phe Ser Thr Glu Trp Trp Cys
             35                  40                  45

Asp Pro Ser Tyr Gly Leu Ser Asp Ala Gly Tyr Gly Tyr Cys Phe Val
 50                  55                  60

Glu Ala Thr Gly Gly Tyr Leu Val Val Gly Val Glu Lys Lys Gln Ala
 65                  70                  75                  80
```

```
Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
        275                 280                 285

Ile Gly His Ser Ile Cys Asp Ile Ile Ala Lys Glu Phe Trp Thr Phe
290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
                325                 330                 335

Glu Val Glu Glu Phe Val Glu Glu Asp Glu Asp Thr Val
            340                 345                 350

<210> SEQ ID NO 3
<211> LENGTH: 1050
<212> TYPE: DNA
<213> ORGANISM: Artificial Sequence
<220> FEATURE:
<223> OTHER INFORMATION: Synthetic Oligonucleotide

<400> SEQUENCE: 3
atggctgagc tgatcagcag cgccaccaga tctctgtttg ccgccggagg catcaaccct    60
tggcctaacc cctaccacca cgaggacatg ggctgtggag gaatgacacc tacaggcgag   120
tgcttcagca ccgagtggtg gtgtgaccct tcttacggac tgagcgacgc cggatacgga   180
tattgcttcg tggaggccac aggcggctac ctggtcgtgg gagtggagaa gaagcaggct   240
tggctgcaca gcagaggcac accaggagaa aagatcggcg cccaggtctg ccagtggatt   300
gctttcagca tcgccatcgc cctgctgaca ttctacggct cagcgcctg aaggccact    360 tgcggttggg aggaggtcta cgtctgtttg ctcgaggtgc tgttcgtgac cctggagatc   420
ttcaaggagt tcagcagccc cgccacagtg tacctgtcta ccggcaacca cgcctattgc   480
ctgcgctact cgagtggct gctgtcttgc cccgtgatcc tgatcaagct gagcaacctg   540
```

```
agcggcctga agaacgacta cagcaagcgg accatgggcc tgatcgtgtc ttgcgtggga    600
atgatcgtgt tcggcatggc cgcaggactg gctaccgatt ggctcaagtg gctgctgtat    660
atcgtgtctt gcatctacgg cggctacatg tacttccagg ccgccaagtg ctacgtggaa    720
gccaaccaca gcgtgcctaa aggccattgc cgcatggtcg tgaagctgat ggcctacgct    780
tacttcgcct cttggggcag ctacccaatc ctctgggcag tgggaccaga aggactgctg    840
aagctgagcc cttacgccaa cagcatcggc cacagcatct gcacatcat cgccaaggag    900 ttttggacct tcctggccca ccacctgagg atcaagatcc acgagcacat cctgatccac    960
ggcgacatcc ggaagaccac caagatggag atcggaggcg aggaggtgga agtggaagag    1020
ttcgtggagg aggaggacga ggacacagtg                                     1050
```

<210> SEQ ID NO 4
<211> LENGTH: 235
<212> TYPE: PRT
<213> ORGANISM: Chlamydomonas noctigama

<400> SEQUENCE: 4

```
Gly Thr Pro Gly Glu Lys Ile Gly Ala Gln Val Cys Gln Trp Ile Ala
1               5                   10                  15

Phe Ser Ile Ala Ile Ala Leu Leu Thr Phe Tyr Gly Phe Ser Ala Trp
            20                  25                  30

Lys Ala Thr Cys Gly Trp Glu Glu Val Tyr Val Cys Cys Val Glu Val
        35                  40                  45

Leu Phe Val Thr Leu Glu Ile Phe Lys Glu Phe Ser Ser Pro Ala Thr
    50                  55                  60

Val Tyr Leu Ser Thr Gly Asn His Ala Tyr Cys Leu Arg Tyr Phe Glu
65                  70                  75                  80

Trp Leu Leu Ser Cys Pro Val Ile Leu Ile Lys Leu Ser Asn Leu Ser
                85                  90                  95

Gly Leu Lys Asn Asp Tyr Ser Lys Arg Thr Met Gly Leu Ile Val Ser
            100                 105                 110

Cys Val Gly Met Ile Val Phe Gly Met Ala Ala Gly Leu Ala Thr Asp
        115                 120                 125

Trp Leu Lys Trp Leu Leu Tyr Ile Val Ser Cys Ile Tyr Gly Gly Tyr
    130                 135                 140

Met Tyr Phe Gln Ala Ala Lys Cys Tyr Val Glu Ala Asn His Ser Val
145                 150                 155                 160

Pro Lys Gly His Cys Arg Met Val Val Lys Leu Met Ala Tyr Ala Tyr
                165                 170                 175

Phe Ala Ser Trp Gly Ser Tyr Pro Ile Leu Trp Ala Val Gly Pro Glu
            180                 185                 190

Gly Leu Leu Lys Leu Ser Pro Tyr Ala Asn Ser Ile Gly His Ser Ile
        195                 200                 205

Cys Asp Ile Ile Ala Lys Glu Phe Trp Thr Phe Leu Ala His His Leu
    210                 215                 220

Arg Ile Lys Ile His Glu His Ile Leu Ile His
225                 230                 235
```

<210> SEQ ID NO 5
<211> LENGTH: 346
<212> TYPE: PRT
<213> ORGANISM: Artificial Sequence
<220> FEATURE:
<223> OTHER INFORMATION: Synthetic Polypeptide

<400> SEQUENCE: 5

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
        35                  40                  45

Phe Asp Glu Leu Ala Lys Gly Ala Val Val Pro Glu Asp His Phe Val
    50                  55                  60

Cys Gly Pro Ala Asp Lys Cys Tyr Cys Ser Ala Trp Leu His Ser His
65                  70                  75                  80

Gly Ser Lys Glu Glu Lys Thr Ala Phe Thr Val Met Gln Trp Ile Val
                85                  90                  95

Phe Ala Val Cys Ile Ile Ser Leu Leu Phe Tyr Ala Tyr Gln Thr Trp
            100                 105                 110

Arg Ala Thr Cys Gly Trp Glu Glu Val Tyr Val Thr Ile Ile Glu Leu
        115                 120                 125

Val His Val Cys Phe Gly Leu Trp His Glu Val Asp Ser Pro Cys Thr
    130                 135                 140

Leu Tyr Leu Ser Thr Gly Asn Met Val Leu Trp Leu Arg Tyr Ala Glu
145                 150                 155                 160

Trp Leu Leu Thr Cys Pro Val Ile Leu Ile His Leu Ser Asn Leu Thr
                165                 170                 175

Gly Met Lys Asn Asp Tyr Asn Lys Arg Thr Met Ala Leu Leu Val Ser
            180                 185                 190

Asp Val Gly Cys Ile Val Trp Gly Thr Thr Ala Ala Leu Ser Thr Asp
        195                 200                 205

Phe Val Lys Ile Ile Phe Phe Phe Leu Gly Leu Leu Tyr Gly Phe Tyr
    210                 215                 220

Thr Phe Tyr Ala Ala Ala Lys Ile Tyr Ile Glu Ala Tyr His Thr Val
225                 230                 235                 240

Pro Lys Gly Ile Cys Arg Gln Leu Val Arg Leu Gln Ala Tyr Asp Phe
                245                 250                 255

Phe Phe Thr Trp Ser Met Phe Pro Ile Leu Phe Met Val Gly Pro Glu
            260                 265                 270

Gly Phe Gly Lys Ile Thr Ala Tyr Ser Ser Gly Ile Ala His Glu Val
        275                 280                 285

Cys Asp Leu Leu Ser Lys Asn Leu Trp Gly Leu Met Gly His Phe Ile
    290                 295                 300

Arg Val Lys Ile His Glu His Ile Leu Val His Gly Asn Ile Thr Lys
305                 310                 315                 320

Lys Thr Lys Val Asn Val Ala Gly Asp Met Val Glu Leu Asp Thr Tyr
                325                 330                 335

Val Asp Gln Asp Glu His Asp Glu Gly
            340                 345

<210> SEQ ID NO 6
<211> LENGTH: 79
<212> TYPE: PRT
<213> ORGANISM: Chlamydomonas noctigama

<400> SEQUENCE: 6

Met Ser Arg Leu Val Ala Ala Ser Trp Leu Leu Ala Leu Leu Leu Cys
1               5                   10                  15

```
Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
        35                  40                  45

Phe Asp Glu Leu Ala Lys Gly Ala Val Val Pro Glu Asp His Phe Val
    50                  55                  60

Cys Gly Pro Ala Asp Lys Cys Tyr Cys Ser Ala Trp Leu His Ser
65                  70                  75

<210> SEQ ID NO 7
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 7
gtcccgtgca cgctgctcct gctgttggca gccgccctgg ctccgactca gacgcgggcc    60

<210> SEQ ID NO 8
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 8

Met Val Pro Cys Thr Leu Leu Leu Leu Ala Ala Ala Leu Ala Pro
1               5                   10                  15

Thr Gln Thr Arg Ala
            20

<210> SEQ ID NO 9
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 9
ttctgctacg agaatgaagt g                                              21

<210> SEQ ID NO 10
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 10

Phe Cys Tyr Glu Asn Glu Val
1               5

<210> SEQ ID NO 11
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 11
aaatccagaa ttacttctga aggggagtat atccctctgg atcaaataga catcaatgtt    60
```

<210> SEQ ID NO 12
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 12

Lys Ser Arg Ile Thr Ser Glu Gly Glu Tyr Ile Pro Leu Asp Gln Ile
1               5                   10                  15

Asp Ile Asn Val
            20

<210> SEQ ID NO 13
<211> LENGTH: 1035
<212> TYPE: DNA
<213> ORGANISM: Artificial Sequence
<220> FEATURE:
<223> OTHER INFORMATION: Synthetic Oligonucleotide

<400> SEQUENCE: 13
atgagcagac tggtcgccgc ttcttggctg ctggctctcc tcctctgcgg aattaccagc      60
acaacaacag cctctagcgc cccagcagct tcttctacag acggaacagc cgccgcagca     120
gtgtctcact acgccatgaa cggcttcgac gagctggcta aggagccgt  ggtgccagaa     180 gaccactttg tctgcggacc agccgacaag tgctattgct ccgcttggct gcacagcaga     240
ggcacaccag agaaaagat  cggcgcccag gtctgccagt ggattgcttt cagcatcgcc     300
atcgccctgc tgacattcta cggcttcagc gcctggaagg ccacttgcgg ttgggaggag     360
gtctacgtct gttgcgtcga ggtgctgttc gtgaccctgg atcttcaa  ggagttcagc     420 agccccgcca cagtgtacct gtctaccggc aaccacgcct attgcctgcg ctacttcgag     480
tggctgctgt cttgccccgt gatcctgatc aagctgagca acctgagcgg cctgaagaac     540
gactacagca gcggaccat  gggcctgatc gtgtcttgcg tgggaatgat cgtgttcggc     600
atggccgcag actggctac  cgattggctc aagtggctgc tgtatatcgt gtcttgcatc     660
tacggcggct acatgtactt ccaggccgcc aagtgctacg tggaagccaa ccacagcgtg     720
cctaaaggcc attgccgcat ggtcgtgaag ctgatggcct acgcttactt cgcctcttgg     780
ggcagctacc caatcctctg ggcagtggga ccagaaggac tgctgaagct gagcccttac     840
gccaacagca tcggcacag  catctgcgac atcatcgcca aggagttttg gaccttcctg     900
gcccaccacc tgaggatcaa gatccacgag cacatcctga tccacggcga catccggaag     960
accaccaaga tggagatcgg aggcgaggag gtggaagtgg aagagttcgt ggaggaggag    1020
gacgaggaca cagtg                                                     1035

<210> SEQ ID NO 14
<211> LENGTH: 1038
<212> TYPE: DNA
<213> ORGANISM: Artificial Sequence
<220> FEATURE:
<223> OTHER INFORMATION: Synthetic Oligonucleotide

<400> SEQUENCE: 14
atgagcagac tggtcgccgc ttcttggctg ctggctctcc tcctctgcgg aattaccagc      60
acaacaacag cctctagcgc cccagcagct tcttctacag acggaacagc cgccgcagca     120
gtgtctcact acgccatgaa cggcttcgac gagctggcta aggagccgt  ggtgccagaa     180 gaccactttg tctgcggacc agccgacaag tgctattgct ccgcttggct gcacagccac     240

```
ggaagcaagg aggagaagac cgccttcacc gtcatgcagt ggatcgtgtt cgccgtctgc      300
atcatcagcc tgctgttcta cgcctaccag acttggaggg ctacttgcgg ttgggaggag      360
gtgtacgtga ccatcatcga gctggtccac gtctgcttcg gactctggca cgaggtcgat      420
agcccttgta ccctgtacct gagcacaggc aacatggtcc tctggctgag atacgccgag      480
tggctgctga cttgccccgt gatcctgatc cacctgagca acctgaccgg catgaagaac      540
gactacaaca gcggaccat ggccctgctg gtgtcagacg tgggctgtat cgtgtgggga      600
acaacagccg ccctgagcac cgatttcgtg aagatcatct tcttcttcct gggcctgctg      660
tacggcttct acaccttcta cgccgccgcc aagatctaca tcgaggccta ccacaccgtg      720
cccaagggca tttgtagaca gctcgtgcgg ctgcaggcct acgacttctt cttcacttgg      780
agcatgttcc ccatcctgtt catggtcggc cagagggat tcggcaagat caccgcctac      840
agcagcggaa tcgcccacga agtgtgcgat ctgctgagca agaacctctg gggcctgatg      900
ggccacttca tccgcgtgaa gatccacgag cacatcctgg tgcacggcaa catcaccaag      960
aagaccaagg tcaacgtggc cggcgacatg gtggaactgg acacctacgt ggaccaggac     1020
gaggaacacg acgaggga                                                   1038

<210> SEQ ID NO 15
<211> LENGTH: 237
<212> TYPE: DNA
<213> ORGANISM: Artificial Sequence
<220> FEATURE:
<223> OTHER INFORMATION: Synthetic Oligonucleotide

<400> SEQUENCE: 15
atgagcagac tggtcgccgc ttcttggctg ctggctctcc tcctctgcgg aattaccagc       60
acaacaacag cctctagcgc cccagcagct tcttctacag acggaacagc cgccgcagca      120
gtgtctcact acgccatgaa cggcttcgac gagctggcta aggagccgt ggtgccagaa       180 gaccactttg tctgcggacc agccgacaag tgctattgct ccgcttggct gcacagc         237

<210> SEQ ID NO 16
<211> LENGTH: 345
<212> TYPE: PRT
<213> ORGANISM: Artificial Sequence
<220> FEATURE:
<223> OTHER INFORMATION: Synthetic Polypeptide

<400> SEQUENCE: 16

Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
                20                  25                  30

Thr Asp Gly Thr Ala Ala Ala Val Ser His Tyr Ala Met Asn Gly
            35                  40                  45

Phe Asp Glu Leu Ala Lys Gly Ala Val Val Pro Glu Asp His Phe Val
        50                  55                  60

Cys Gly Pro Ala Asp Lys Cys Tyr Cys Ser Ala Trp Leu His Ser Arg
65                  70                  75                  80

Gly Thr Pro Gly Glu Lys Ile Gly Ala Gln Val Cys Gln Trp Ile Ala
                85                  90                  95

Phe Ser Ile Ala Ile Ala Leu Leu Thr Phe Tyr Gly Phe Ser Ala Trp
            100                 105                 110

Lys Ala Thr Cys Gly Trp Glu Glu Val Tyr Val Cys Cys Val Glu Val
        115                 120                 125
```

Leu Phe Val Thr Leu Glu Ile Phe Lys Glu Phe Ser Ser Pro Ala Thr
    130                 135                 140

Val Tyr Leu Ser Thr Gly Asn His Ala Tyr Cys Leu Arg Tyr Phe Glu
145                 150                 155                 160

Trp Leu Leu Ser Cys Pro Val Ile Leu Ile Arg Leu Ser Asn Leu Ser
                165                 170                 175

Gly Leu Lys Asn Asp Tyr Ser Lys Arg Thr Met Gly Leu Ile Val Ser
            180                 185                 190

Cys Val Gly Met Ile Val Phe Gly Met Ala Ala Gly Leu Ala Thr Asp
        195                 200                 205

Trp Leu Lys Trp Leu Leu Tyr Ile Val Ser Cys Ile Tyr Gly Gly Tyr
210                 215                 220

Met Tyr Phe Gln Ala Ala Lys Cys Tyr Val Glu Ala Asn His Ser Val
225                 230                 235                 240

Pro Lys Gly His Cys Arg Met Val Val Lys Leu Met Ala Tyr Ala Tyr
                245                 250                 255

Phe Ala Ser Trp Gly Ser Tyr Pro Ile Leu Trp Ala Val Gly Pro Glu
            260                 265                 270

Gly Leu Leu Lys Leu Ser Pro Tyr Ala Asn Ser Ile Gly His Ser Ile
        275                 280                 285

Cys Asp Ile Ile Ala Lys Glu Phe Trp Thr Phe Leu Ala His His Leu
290                 295                 300

Arg Ile Lys Ile His Glu His Ile Leu Ile His Gly Asp Ile Arg Lys
305                 310                 315                 320

Thr Thr Lys Met Glu Ile Gly Gly Glu Glu Val Glu Val Glu Glu Phe
                325                 330                 335

Val Glu Glu Glu Asp Glu Asp Thr Val
            340                 345

<210> SEQ ID NO 17
<211> LENGTH: 1035
<212> TYPE: DNA
<213> ORGANISM: Artificial Sequence
<220> FEATURE:
<223> OTHER INFORMATION: Synthetic Oligonucleotide

<400> SEQUENCE: 17
atgagcagac tggtcgccgc ttcttggctg ctggctctcc tcctctgcgg aattaccagc      60
acaacaacag cctctagcgc cccagcagct tcttctacag acggaacagc cgccgcagca     120
gtgtctcact acgccatgaa cggcttcgac gagctggcta aggagccgt ggtgccagaa      180 gaccactttg tctgcggacc agccgacaag tgctattgct ccgcttggct gcacagcaga     240
ggcacaccag agaaaagat cggcgcccag gtctgccagt ggattgcttt cagcatcgcc     300
atcgccctgc tgacattcta cggcttcagc gcctggaagg ccacttgcgg ttgggaggag     360
gtctacgtct gttgcgtcga ggtgctgttc gtgaccctgg agatcttcaa ggagttcagc     420
agccccgcca cagtgtacct gtctaccggc aaccacgcct attgcctgcg ctacttcgag     480
tggctgctgt cttgccccgt gatcctgatc agactgagca acctgagcgg cctgaagaac     540
gactacagca agcggaccat gggcctgatc gtgtcttgcg tgggaatgat cgtgttcggc     600
atggccgcag gactggctac cgattggctc aagtggctgc tgtatatcgt gtcttgcatc     660
tacggcggct acatgtactt ccaggccgcc aagtgctacg tggaagccaa ccacagcgtg     720
cctaaaggcc attgccgcat ggtcgtgaag ctgatggcct acgcttactt cgcctcttgg     780

```
ggcagctacc caatcctctg ggcagtggga ccagaaggac tgctgaagct gagcccttac    840
gccaacagca tcggccacag catctgcgac atcatcgcca aggagttttg gaccttcctg    900
gcccaccacc tgaggatcaa gatccacgag cacatcctga tccacggcga catccggaag    960
accaccaaga tggagatcgg aggcgaggag gtggaagtgg aagagttcgt ggaggaggag   1020
gacgaggaca cagtg                                                    1035
```

US 10,882,892 B2

CHANNELRHODOPSIN VARIANTS AND USES THEREOF

RELATED APPLICATION

This application claims the benefit under 35 U.S.C. § 119(e) of U.S. Provisional application Ser. No. 62/033,213 filed Aug. 5, 2014, the disclosure of which is incorporated by reference herein in its entirety.

GOVERNMENT INTEREST

This invention was made with government support under Contract No. HR0011-12-C-0068 awarded by the Defense Advanced Research Projects Agency, under Grant Nos. OD002002, R01 NS075421, R01 DA029639, MH088182, and under Contract No. R01 NS067199 awarded by the National Institutes of Health, and under Grant Nos. CBET-1053233, DMS-0848804, and EFRI0835878. The United States government has certain rights in the invention.

FIELD OF THE INVENTION

The invention, in some aspects relates to compositions and methods for altering conductance across membranes, cell activity, and cell function, also relates to the use of CsChrimson light-activated ion channels and variants thereof in membranes, cells, tissues, and subjects.

BACKGROUND OF THE INVENTION

Altering and controlling cell membrane and subcellular region ion permeability has permitted examination of characteristics of cells, tissues, and organisms. Light-driven pumps and channels have been used to silence or enhance cell activity and their use has been proposed for drug screening, therapeutic applications, and for exploring cellular and subcellular function.

Molecular-genetic methods for preparing cells that can be activated (e.g., depolarized) or inactivated (e.g., hyperpolarized) by specific wavelengths of light have been developed (see, for example, Han, X. and E. S. Boyden, 2007, PLoS ONE 2, e299). It has been identified that the light-activated cation channel channelrhodopsin-2 (ChR2), and the light-activated chloride pump halorhodopsin (Halo/NpHR), when transgenically expressed in cell such as neurons, make them sensitive to being activated by blue light, and silenced by yellow light, respectively (Han, X. and E. S. Boyden, 2007, PLoS ONE 2(3): e299; Boyden, E. S., et. al., 2005, Nat Neurosci. 2005 September; 8(9): 1263-8. Epub 2005 Aug. 14.). Additional light-activated ion channel polypeptides have been identified, see for example, PCT Publication No. WO2013/071231 and Nature Methods (2014) volume 11(3) 338-346, published online Feb. 9, 2014. Many previously identified light-activated pumps and channels have been restricted to activation by particular wavelengths of light, thus limiting their usefulness.

SUMMARY OF THE INVENTION

The invention, in part, relates to light-activated ion channel polypeptides and methods for their preparation and use. The invention also includes isolated nucleic acid sequences that encode light-driven ion channels of the invention as well as vectors and constructs and cells that comprise such nucleic acid sequences. In addition, the invention in some aspects includes expression of light-activated ion channel polypeptides in cells, tissues, and subjects as well as methods for using the light-activated ion channels to alter conductance across membranes, to alter cell and tissue function, and for use in diagnosis and treatment of disorders, diseases, and conditions.

The invention, in part, also relates to methods for adjusting the voltage potential of cells, subcellular regions, or extracellular regions. Some aspects of the invention include methods of incorporating at least one CsChrimson light-activated ion channel or variant thereof of the invention into at least one target cell, subcellular region, or extracellular region, the ion channel functioning to change transmembrane passage of ions in response to a specific wavelength of light. Exposing an excitable cell that includes an expressed light-driven ion channel of the invention to a wavelength of light that activates the channel, may result in depolarization of the excitable cell. By contacting a cell that includes a light-activated ion channel of the invention with particular wavelengths of light, the cell is depolarized. A plurality of light-activated ion channels activated by different wavelengths of light in overlapping or non-overlapping pluralities of cells may be used to achieve multi-color depolarization.

In some embodiments, the invention comprises a method for the expression of newly identified sequences that encode CsChrimson light-activated ion channels or variants thereof, in genetically targeted cells, to allow millisecond-timescale generation of depolarizing current in response to pulses of light. CsChrimson light-activated channels of the invention can be genetically expressed in specific cells (e.g., using a virus or other means for delivery) and then used to control cells in intact organisms (including humans) as well as cells in vitro, in response to pulses of light. Given that these channels have different activation spectra from other art-known light-activated channels (e.g., ChR2/VChR1, Chronos, etc.), they also allow multiple colors of light to be used to depolarize different sets of cells in the same tissue, by expressing channels with different activation spectra genetically in different cells, and then illuminating the tissue with different colors of light.

The ability to optically perturb, modify, or control cellular function offers many advantages over physical manipulation mechanisms, such as speed, non-invasiveness, and the ability to easily span vast spatial scales from the nanoscale to macroscale. One such approach is an opto-genetic approach, in which light-activated ion channels, including but not limited to CsChrimson light activated ion channels or variants thereof of the invention, are used to move ions with various spectra of light.

According to one aspect of the invention, CsChrimson light-activated ion channel polypeptide or variant comprising an amino acid sequence set forth as SEQ ID NO: 1 or an amino acid sequence having at least 70%, 75%, 80%, 85%, 90%, 95%, or 100% identity to amino acids 1-79 of SEQ ID NO: 1 and at least 85%, 90%, 95%, 96%, 97%, 98%, 99% or 100% identity to amino acids 80-315 of SEQ ID NO: 1 are provided. In some embodiments, activating the ion channel comprises contacting the ion channel polypeptide with a light having a wavelength between 365 nm and 735 nm. In some embodiments, activating the ion channel comprises contacting the ion channel polypeptide with a light having a wavelength from 530 nm to 640 nm, and optionally having a wavelength of 590 nm. In certain embodiments, the nucleic acid sequence encoding the light-activated ion channel polypeptide comprises the nucleic acid sequence set forth as SEQ ID NO: 13. In some embodiments, the CsChrimson light-activated ion channel polypeptide is expressed in a membrane. In some embodiments, the membrane is a vertebrate or invertebrate cell membrane, and optionally is an avian, insect, mammalian, or fish cell membrane. In certain embodiments, the CsChrimson light-activated ion channel polypeptide is expressed in a cell. In some embodiments, the cell is an excitable cell. In certain embodiments the cell is a vertebrate cell, an invertebrate cell, an avian cell, an insect cell, a mammalian cell, or a fish cell. In some embodiments, the cell is in a subject. In some embodiments, the subject is a vertebrate. In certain embodiments, the subject is a mammal. In some embodiments, the subject is a human. In some embodiments, the membrane is a cell membrane of a neuronal cell, a nervous system cell, a cardiac cell, a circulatory system cell, a visual system cell, or an auditory system cell. In some embodiments, altering the ion conductivity of the membrane depolarizes the cell.

According to another aspect of the invention, methods of altering ion conductivity of a membrane are provided. The methods including a) expressing in a host membrane a CsChrimson light-activated ion channel polypeptide or variant thereof of any one of aforementioned embodiments and b) contacting the CsChrimson light-activated ion channel polypeptide or variant thereof with a light under suitable conditions to activate the light-activated ion channel and alter the ion conductivity of the membrane. In certain embodiments, the activating light has a wavelength from 365 nm to 735 nm, and optionally, the activating light has a wavelength of 590 nm. In some embodiments, the host membrane is in cell. In some embodiments, the cell is a neuronal cell and the method additionally includes contacting the CsChrimson light-activated ion channel polypeptide or variant thereof with a light having a wavelength up to 735 nm under conditions suitable to produce a spike in the neuronal cell. In certain embodiments, the membrane is cell membrane. In some embodiments, the cell is a vertebrate cell, an invertebrate cell, an avian cell, an insect cell, a mammalian cell, or a fish cell. In some embodiments, the cell is in a subject. In certain embodiments, the subject is a vertebrate. In some embodiments, the subject is a mammal. In some embodiments, the subject is a human. In some embodiments, the membrane is a cell membrane of a neuronal cell, a nervous system cell, a cardiac cell, a circulatory system cell, a visual system cell, or an auditory system cell. In certain embodiments, altering the ion conductivity of the membrane depolarizes the cell. In some embodiments, the nucleic acid sequence encoding the CsChrimson light-activated ion channel polypeptide comprises the nucleic acid sequence set forth as SEQ ID NO: 13. In some embodiments, the amino acid sequence of the light-activated ion channel polypeptide comprises the sequence set forth as SEQ ID NO: 1.

According to yet another aspect of the invention, methods of assessing the effect of a candidate compound on ion conductivity of a membrane are provided. The methods include contacting a test membrane comprising the isolated light-activated ion channel polypeptide of any one of the aforementioned embodiments with light under conditions suitable for altering ion conductivity of the test membrane; b) contacting the test membrane with a candidate compound; and c) identifying the presence or absence of a change in ion conductivity of the test membrane contacted with the light and the candidate compound compared to ion conductivity of a membrane of a control membrane contacted with the light and not contacted with the candidate compound; wherein a change in the ion conductivity of the test membrane compared to the control indicates an effect of the candidate compound on the ion conductivity of the test membrane. In some embodiments, the membrane is in a cell.

In certain embodiments, the cell is a vertebrate cell, an invertebrate cell, an avian cell, an insect cell, a mammalian cell, or a fish cell. In some embodiments, the cell is in a subject. In some embodiments, the subject is a vertebrate. In some embodiments, the subject is a mammal. In certain embodiments, altering the ion conductivity of the membrane depolarizes the cell. In some embodiments, the change in the ion conductivity is an increase in ion conductivity of the membrane. In some embodiments, the change in the ion conductivity is a decrease in ion conductivity of the membrane.

According to yet another aspect of the invention, methods of treating a disease or condition in a subject are provided. The methods include (a) administering to a subject in need of such treatment, a therapeutically effective amount of a CsChrimson light-activated ion channel polypeptide or variant thereof of any one of and aforementioned embodiments, to treat the disease or condition; (b) expressing the CsChrimson light-activated ion channel polypeptide or variant thereof in a cell membrane of the subject; and (c) contacting the cell with light and activating the light-activated ion channel in the cell under conditions sufficient to alter ion conductivity of the cell membrane, wherein altering the conductivity of the cell membrane treats the disease or condition. In some embodiments, altering the ion conductivity of the membrane depolarizes the cell. In certain embodiments, the disease or condition is injury, brain damage, spinal cord injury, epilepsy, a metabolic disorder, cardiac dysfunction, vision loss, blindness, deafness, hearing loss, or a neurological condition. In some embodiments, the subject is a vertebrate. In some embodiments, the subject is a mammal. In certain embodiments, the subject is a human. In some embodiments, the cell is a vertebrate cell, an invertebrate cell, an avian cell, an insect cell, a mammalian cell, or a fish cell. In some embodiments, the membrane is a cell membrane of a neuronal cell, a nervous system cell, a cardiac cell, a circulatory system cell, a visual system cell, or an auditory system cell.

According to another aspect of the invention, methods of performing a multi-color light ion channel activation assay in a population of cells are provided. The methods include (a) expressing a blue-light-activated ion channel in a first subpopulation of a population of cells; (b) expressing a CsChrimson light-activated ion channel polypeptide or variant thereof of any one of the aforementioned embodiments in a second subpopulation of the population of cells, wherein the first and second subpopulations are non-overlapping subpopulations; (c) contacting the population of cells with a plurality of blue light test doses comprising combinations of blue light wavelength, pulse width, and power; (d) measuring transmembrane voltage deflection in a cell of the second subpopulation of cells contacted with the blue light test doses; (e) determining the test blue light dose comprising a maximum blue light power that activates the blue-light activated ion channel in first subpopulation of cells and results in a minimum sub-threshold transmembrane voltage deflection in the second subpopulation of cells; (f) contacting the population of cells with a plurality of blue light test doses comprising a lower power than the maximum blue light power of (e); (g) determining the blue light test doses of (f) that activate the blue-light activated ion channel; (h) contacting the population of cells with a plurality of red light test doses comprising combinations of red light wavelength, pulse width, and power, (i) determining a red light test dose comprising a red light power that activates the second subpopulation of cells; and (j) performing an activity assay comprising contacting the population of cells with the blue light test dose determined in (g) and the red light test dose determined in (i). In certain embodiments, the plurality of blue light test doses comprise wavelengths, pulse widths, and powers independently selected from between 400 nm and 500 nm, 1 ms and 5 ms, and 10 μW/mm$^2$ and 1.0 mW/mm$^2$, respectively. In some embodiments, the red light test dose of (i) is the test dose comprising a minimum red light power that activates the second population of cells. In some embodiments, measuring the transmembrane voltage deflection in (d) comprises patch clamping a cell of the second population of cells and determining one or more voltage changes in the cell. In some embodiments, the determining in (e) comprises altering the blue light dose by increasing the blue light power from 0.5 mW/mm$^2$ to 10 mW/mm$^2$; and measuring the sub-threshold transmembrane voltage deflection in the second subpopulation of cells. In certain embodiments, the minimum sub-threshold voltage deflection is less than 15 mV, less than 10 mV, or less than 5 mV. In some embodiments, the maximum blue light power in (e) is between 0.4 mW/mm$^2$ and 0.6 mW/mm$^2$. In some embodiments, the blue light power in (g) is between 50 μW/mm$^2$ and 0.4 mW/mm$^2$. In some embodiments, the nucleic acid sequence encoding the CsChrimson light-activated ion channel polypeptide comprises the nucleic acid sequence set forth as SEQ ID NO: 13. In certain embodiments, the cell is a vertebrate cell, an invertebrate cell, an avian cell, an insect cell, a mammalian cell, or a fish cell.

According to yet another aspect of the invention, a nucleic acid sequence that encodes a CsChrimson light-activated ion channel polypeptide or variant thereof of any one of the aforementioned embodiments is provided. According to yet another aspect of the invention, constructs that include a nucleic acid sequence of any one of the aforementioned embodiments is provided. In some embodiments, the construct also includes at least one nucleic acid sequence that encodes a trafficking polypeptide. In some embodiments, the construct also includes at least one nucleic acid sequence that encodes a fluorescent polypeptide. In some embodiments, the at least one trafficking polypeptide is ER2 or KGC. In certain embodiments, the at least one fluorescent polypeptide is GFP or Venus.

BRIEF DESCRIPTION OF THE DRAWINGS

FIG. 1A provides a schematic of CsChrimson, which is a chimera that includes portions of two unrelated polypeptides. CsChR region is at N terminal above the diagrammed membrane. FIG. 1B provides an action spectrum for Chrimson and CsChrimson, as well as the Chrimson spectrum data from previous work [see PCT Publication No. WO2013/071231 and Nature Methods (2014) volume 11(3) 338-346, published online Feb. 9, 2014], showing HEK293 cells; measured using equal photon fluxes of ~2.5×10$^{21}$ photons/s/m$^2$. FIG. 1C provides a schematic of trafficking sequences used to generate the CsChrimson Drosophila transgenics, that includes CsChrimson, GFP, and sequences KSRITSEGEYIPLDQIDINV (SEQ ID NO: 12) and FCYENEY (SEQ ID NO: 10). FIGS. 1D-E show traces indicating maximum photocurrents in response to red (625-nm) and far-red (735-nm) light as measured in cultured neurons containing various Chrimson and CsChrimson constructs. FIGS. 1F-G are graphs illustrating the Turn-on kinetics (FIG. 1F) and recovery kinetics (FIG. 1G) in response to 735-nm light. CsChrimson kinetic data were pooled from all trafficking versions. All constructs in this panel were expressed under CaMKII promoter and selected based solely on the presence of co-transfected cytosolic tdTomato expression. Illumination conditions are as labeled in each panel. Box plot whiskers represent minimum and maximum data points. Box limits represent 25$^{th}$ percentile, median, and 75$^{th}$ percentile. Statistics: n=7 to 12 cells for all constructs except for CsChrimson-GFP-ER2, which has n=4 cells in FIG. 1D and n=3 cells in FIG. 1E. Plotted data are mean±s.e.m. in FIGS. 1B, 1F, and 1G. ANOVA with Dunnett's post hoc test with Chrimson-GFP as reference in FIGS. 1D and 1E.

BRIEF DESCRIPTION OF THE SEQUENCES

Figure 1A:
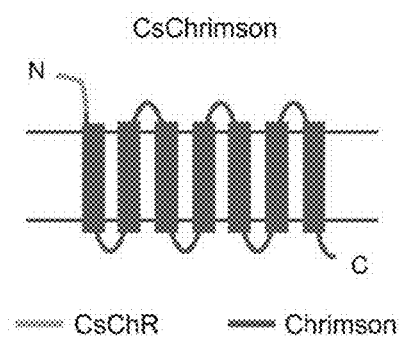
FIGS. 1A-G show results of CsChrimson characterization in cultured cells.

```
SEQ ID NO: 1 is the amino acid sequence of
CsChrimson
MSRLVAASWLLALLLCGITSTTTASSAPAASSTDGTAAAAVSHYAMNGF

DELAKGAVVPEDHFVCGPADKCYCSAWLHSRGTPGEKIGAQVCQWIAFS

IAIALLTFYGFSAWKATCGWEEVYVCCVEVLFVTLEIFKEFSSPATVYL

STGNHAYCLRYFEWLLSCPVILIKLSNLSGLKNDYSKRTMGLIVSCVGM

IVFGMAAGLATDWLKWLLYIVSCIYGGYMYFQAAKCYVEANHSVPKGHC

RMVVKLMAYAYFASWGSYPILWAVGPEGLLKLSPYANSIGHSICDIIAK

EFWTFLAHHLRIKIHEHILIHGDIRKTTKMEIGGEEVEVEEFVEEEDED

TV.

SEQ ID NO: 2 is the amino acid sequence of
Chrimson ,also referred to herein as ChR88
MAELISSATRSLFAAGGINPWPNPYHHEDMGCGGMTPTGECFSTEWWCD

PSYGLSDAGYGYCFVEATGGYLVVGVEKKQAWLHSRGTPGEKIGAQVCQ

WIAFSIAIALLTFYGFSAWKATCGWEEVYVCCVEVLFVTLEIFKEFSSP

ATVYLSTGNHAYCLRYFEWLLSCPVILIKLSNLSGLKNDYSKRTMGLIV

SCVGMIVFGMAAGLATDWLKWLLYIVSCIYGGYMYFQAAKCYVEANHSV

PKGHCRMVVKLMAYAYFASWGSYPILWAVGPEGLLKLSPYANSIGHSIC

DIIAKEFWTFLAHHLRIKIHEHILIHGDIRKTTKMEIGGEEVEVEEFVE

EEDEDTV.

SEQ ID NO: 3 is a mammalian-codon optimized DNA
sequence encoding ChR88 light-activated ion
channel polypeptide
atggctgagctgatcagcagcgccaccagatctctgtttgccgccgag gcatcaaccttggcctaaccctaccaccacgaggacatgggctgtgg
```

```
aggaatgacacctacaggcgagtgcttcagcaccgagtggtggtgtgac ccttcttacggactgagcgacgccggatacggatattgcttcgtggagg ccacaggcggctacctggtcgtgggagtggagaagaagcaggcttggct gcacagcagaggcacaccaggagaaaagatcggcgcccaggtctgccag tggattgctttcagcatcgccatcgccctgctgacattctacggcttca gcgcctggaaggccacttgcggttgggaggaggtctacgtctgttgcgt cgaggtgctgttcgtgaccctggagatcttcaaggagttcagcagcccc gccacagtgtacctgtctaccggcaaccacgcctattgcctgcgctact tcgagtggctgctgtcttgccccgtgatcctgatcaagctgagcaacct gagcggcctgaagaacgactacagcaagcggaccatgggcctgatcgtg tcttgcgtgggaatgatcgtgttcggcatggccgcaggactggctaccg attggctcaagtggctgctgtatatcgtgtcttgcatctacggcggcta catgtacttccaggccgccaagtgctacgtggaagccaaccacagcgtg cctaaaggccattgccgcatggtcgtgaagctgatggcctacgcttact tcgcctcttggggcagctacccaatcctctgggcagtgggaccagaagg actgctgaagctgagcccttacgccaacagcatcggccacagcatctgc gacatcatcgccaaggagttttggaccttcctggcccaccacctgagga tcaagatccacgagcacatcctgatccacggcgacatccggaagaccac caagatggagatcggaggcgaggaggtggaagtggaagagttcgtggag gaggaggacgaggacacagtg SEQ ID NO: 4 is transmembrane region of ChR88
including residues 86-320 of SEQ ID NO: 2
GTPGEKIGAQVCQWIAFSIAIALLTFYGFSAWKATCGWEEVYVCCVEVL

FVTLEIFKEFSSPATVYLSTGNHAYCLRYFEWLLSCPVILIKLSNLSGL

KNDYSKRTMGLIVSCVGMIVFGMAAGLATDWLKWLLYIVSCIYGGYMYF

QAAKCYVEANHSVPKGHCRMVVKLMAYAYFASWGSYPILWAVGPEGLLK

LSPYANSIGHSICDIIAKEFWTFLAHHLRIKIHEHILIH.

SEQ ID NO: 5 amino acid sequence of CsChR
polypeptide
MSRLVAASWLLALLLCGITSTTTASSAPAASSTDGTAAAAVSHYAMNGF

DELAKGAVVPEDHFVCGPADKCYCSAWLHSHGSKEEKTAFTVMQWIVFA

VCIISLLFYAYQTWRATCGWEEVYVTIIELVHVCFGLWHEVDSPCTLYL

STGNMVLWLRYAEWLLTCPVILIHLSNLTGMKNDYNKRTMALLVSDVGC

IVWGTTAALSTDFVKIIFFFLGLLYGFYTFYAAAKIYIEAYHTVPKGIC

RQLVRLQAYDFFFTWSMFPILFMVGPEGFGKITAYSSGIAHEVCDLLSK

NLWGLMGHFIRVKIHEHILVHGNITKKTKVNVAGDMVELDTYVDQEEH

DEG.

SEQ ID NO: 6 the amino acid sequence of a CsChR
N-terminal fragment including residues 1-79 of
SEQ ID NO: 5
MSRLVAASWLLALLLCGITSTTTASSAPAASSTDGTAAAAVSHYAMNGF
DELAKGAVVPEDHFVCGPADKCYCSAWLHS.

SEQ ID NO: 7 is the DNA sequence of the 'ss'
signal sequence from truncated MHC class I
antigen:
gtcccgtgcacgctgctcctgctgttggcagccgccctggctccgactc
agacgcgggcc.

SEQ ID NO: 8 is the amino acid sequence of the
'ss' signal sequence from truncated MHC class
I antigen:
MVPCTLLLLLAAALAPTQTRA.

SEQ ID NO: 9 is the DNA sequence of the ER export
sequence (also referred to herein as "ER2"):
ttctgctacgagaatgaagtg.

SEQ ID NO: 10 is the amino acid sequence of the
ER export sequence (also referred to herein as
"ER2"):
FCYENEV.

SEQ ID NO: 11 is the DNA sequence of KGC, which
is a C terminal export sequence from the
potassium channel Kir2.1:
aaatccagaattacttctgaaggggagtatatccctctggatcaaataga
catcaatgtt.

SEQ ID NO: 12 is the amino acid sequence of KGC,
which is a C terminal export sequence from the
potassium channel Kir2.1:
KSRITSEGEYIPLDQIDINV.

SEQ ID NO: 13 is the nucleic acid sequence
encoding CsChrimson polypeptide set forth herein
as SEQ ID NO: 1.
atgagcagactggtcgccgcttcttggctgctggctctcctcctctgcg gaattaccagcacaacaacagcctctagcgccccagcagcttcttctac agacggaacagccgccgcagcagtgtctcactacgccatgaacggcttc gacgagctggctaaaggagccgtggtgccagaagaccactttgtctgcg gaccagccgacaagtgctattgctccgcttggctgcacagcagaggcac accaggagaaaagatcggcgcccaggtctgccagtggattgctttcagc atcgccatcgccctgctgacattctacggcttcagcgcctggaaggca cttgcggttgggaggaggtctacgtctgttgcgtcgaggtgctgttcgt gaccctggagatcttcaaggagttcagcagccccgccacagtgtacctg tctaccggcaaccacgcctattgcctgcgctacttcgagtggctgctgt cttgccccgtgatcctgatcaagctgagcaacctgagcggcctgaagaa cgactacagcaagcggaccatgggcctgatcgtgtcttgcgtgggaatg atcgtgttcggcatggccgcaggactggctaccgattggctcaagtggc tgctgtatatcgtgtcttgcatctacggcggctacatgtacttccaggc cgccaagtgctacgtggaagccaaccacagcgtgcctaaaggccattgc cgcatggtcgtgaagctgatggcctacgcttacttcgcctcttggggca gctacccaatcctctgggcagtgggaccagaaggactgctgaagctgag cccttacgccaacagcatcggccacagcatctgcgacatcatcgccaag gagttttggaccttcctggcccaccacctgaggatcaagatccacgagc acatcctgatccacggcgacatccggaagaccaccaagatggagatcgg aggcgaggaggtggaagtggaagagttcgtggaggaggaggacgaggac acagtg.
```

SEQ ID NO: 14 is nucleic acid sequence encoding the CsChR polypeptide set forth herein as SEQ ID NO: 5.
atgagcagactggtcgccgcttcttggctgctggctctcctcctctgcg gaattaccagcacaacaacagcctctagcgccccagcagcttcttctac agacggaacagccgccgcagcagtgtctcactacgccatgaacggcttc gacgagctggctaaaggagccgtggtgccagaagaccactttgtctgcg gaccagccgacaagtgctattgctccgcttggctgcacagccacggaag caaggaggagaagaccgccttcaccgtcatgcagtggatcgtgttcgcc gtctgcatcatcagcctgctgttctacgcctaccagacttggagggcta cttgcggttgggaggaggtgtacgtgaccatcatcgagctggtccacgt ctgcttcggactctggcacgaggtcgatagcccttgtaccctgtacctg agcacaggcaacatggtcctctggctgagatacgccgagtggctgctga cttgccccgtgatcctgatccacctgagcaacctgaccggcatgaagaa cgactacaacaagcggaccatggccctgctggtgtcagacgtgggctgt atcgtgtggggaacaacagccgccctgagcaccgatttcgtgaagatca tcttcttcttcctgggcctgctgtacggcttctacaccttctacgccgc cgccaagatctacatcgaggcctaccacaccgtgcccaagggcatttgt agacagctcgtgcggctgcaggcctacgacttcttcttcacttggagca tgttccccatcctgttcatggtcggcccagagggattcggcaagatcac cgcctacagcagcggaatcgcccacgaagtgtgcgatctgctgagcaag aacctctgggcctgatgggccacttcatccgcgtgaagatccacgagc acatcctggtgcacggcaacatcaccaagaagaccaaggtcaacgtggc cggcgacatggtggaactggacacctacgtggaccaggacgaggaacac gacgaggga.

SEQ ID NO: 15 is nucleic acid sequence encoding the CsChR polypeptide N-terminal fragment set forth as SEQ ID NO: 6.
atgagcagactggtcgccgcttcttggctgctggctctcctcctctgcg gaattaccagcacaacaacagcctctagcgccccagcagcttcttctac agacggaacagccgccgcagcagtgtctcactacgccatgaacggcttc gacgagctggctaaaggagccgtggtgccagaagaccactttgtctgcg gaccagccgacaagtgctattgctccgcttggctgcacagc.

SEQ ID NO: 16 is the amino acid sequence of a CsChrimson variant light-activated ion channel polypeptide.
MSRLVAASWLLALLLCGITSTTTASSAPAASSTDGTAAAAVSHYAMNGF

DELAKGAVVPEDHFVCGPADKCYCSAWLHSRGTPGEKIGAQVCQWIAFS

IAIALLTFYGFSAWKATCGWEEVYVCCVEVLFVTLEIFKEFSSPATVYL

STGNHAYCLRYFEWLLSCPVILIRLSNLSGLKNDYSKRTMGLIVSCVGM

IVFGMAAGLATDWLKWLLYIVSCIYGGYMYFQAAKCYVEANHSVPKGHC

RMVVKLMAYAYFASWGSYPILWAVGPEGLLKLSPYANSIGHSICDIIAK

EFWTFLAHHLRIKIHEHILIHGDIRKTTKMEIGGEEVEVEEFVEEEDED

TV.

SEQ ID NO: 17 is nucleic acid sequence that encodes the CsChrimson variant light-activated ion channel polypeptide set forth as SEQ ID NO: 16.
atgagcagactggtcgccgcttcttggctgctggctctcctcctctgcg gaattaccagcacaacaacagcctctagcgccccagcagcttcttctac agacggaacagccgccgcagcagtgtctcactacgccatgaacggcttc gacgagctggctaaaggagccgtggtgccagaagaccactttgtctgcg gaccagccgacaagtgctattgctccgcttggctgcacagcagaggcac accaggagaaagatcggcgcccaggtctgccagtggattgctttcagc atcgccatcgccctgctgacattctacggcttcagcgcctggaaggcca cttgcggttgggaggaggtctacgtctgttgcgtcgaggtgctgttcgt gaccctggagatcttcaaggagttcagcagccccgccacagtgtacctg tctaccggcaaccacgcctattgcctgcgctacttcgagtggctgctgt cttgccccgtgatcctgatcagactgagcaacctgagcggcctgaagaa cgactacagcaagcggaccatgggcctgatcgtgtcttgcgtgggaatg atcgtgttcggcatggccgcaggactggctaccgattggctcaagtggc tgctgtatatcgtgtcttgcatctacggcggctacatgtacttccaggc cgccaagtgctacgtggaagccaaccacagcgtgcctaaaggccattgc cgcatggtcgtgaagctgatggcctacgcttacttcgcctcttgggca gctaccaatcctctgggcagtgggaccagaaggactgctgaagctgag ccctttacgccaacagcatcggccacagcatctgcgacatcatcgccaag gagttttggaccttcctggcccaccacctgaggatcaagatccacgagc acatcctgatccacggcgacatccggaagaccaccaagatggagatcgg aggcgaggaggtggaagtggaagagttcgtggaggaggaggacgaggac acagtg.

DETAILED DESCRIPTION

The invention in some aspects relates to novel light-activated ion channel polypeptides and nucleic acid sequences that encode the polypeptides. Light-activated ion channel polypeptides of the invention can be expressed in cell membranes and can be activated by contact with one or more pulses of light, which results in strong depolarization of the cell. Light-activated channels of the invention, also referred to herein as light-activated ion channels can be expressed in specific cells, tissues, and/or organisms and used to control ion flow and/or excitation in cells in vivo, ex vivo, and in vitro in response to pulses of light of a suitable wavelength. A CsChrimson light-activated ion channel polypeptide of the invention is a chimeric polypeptide comprising an amino acid sequence derived from a *Chlamydomonas* channelrhodopsin polypeptide sequence referred to herein as Chrimson, which is set forth herein as SEQ ID NO: 2, and an amino acid sequence derived from a *Chloromonas* channelrhodopsin polypeptide sequence referred to herein as CsChR, which is set forth herein as SEQ ID NO: 5.

Some aspects of the invention include methods of preparing and using nucleic acid molecules (which may also be referred to herein as "genes") that encode CsChrimson light-activated ion channels or variants thereof of the invention. The invention, in part, also includes isolated nucleic acids comprising sequences that encode CsChrimson light-activated ion channels or variants thereof of the invention and also may include vectors and constructs that comprise such nucleic acid sequences. A construct of the invention may also include nucleic acid sequences that encode a trafficking molecule, a fluorescent molecule, or other label. Non-limiting examples of trafficking molecules include, ER2, KGC, etc. Non-limiting examples of florescent molecules that may be included in a construct of the invention include GFP, Venus, etc. Additional art-known trafficking sequences and fluorescent molecule sequences may be included in constructs of the invention. In some embodiments the invention includes expression of light-activated ion channel polypeptides encoded by the nucleic acid sequences, in cells, tissues, and organisms. As used herein, the phrases: "light-activated ion channel" and "light-activated channel" are used interchangeably.

CsChrimson light-activated ion channels and variants thereof of the invention can be expressed in a membrane of a cell and are strongly activated by contact with red light. An ion channel is an integral membrane protein that forms a pore through a membrane and assists in establishing and modulating the small voltage gradient that exists across the plasma membrane of all cells. Ion channels are also located in subcellular membranes of organelles such as the endoplasmic reticulum (ER), mitochondria, etc. When a light-activated ion channel of the invention is activated by contacting the cell with appropriate light, the pore opens and permits conductance of ions such as sodium, potassium, calcium, etc. through the pore. Conduction of ions through the pore of a CsChrimson light-activated ion channel or variant thereof of the invention may also be referred to herein as the conductivity of the membrane that includes the pore. As used herein, an increase in conductivity of a membrane means an increase in conduction of ions through an ion channel pore in the membrane and a decrease in conductivity of a membrane means a decrease in conduction of ions through an ion channel pore in the membrane. In certain embodiments of the invention, a CsChrimson light-activated ion channel or variant thereof that is present in a membrane may be contacted with a suitable dose of light to activate the ion channel, and an increase in conductivity of the membrane may result. In certain embodiments of the invention, a CsChrimson light-activated ion channel or variant thereof may be expressed in a cell membrane and contacted with a suitable dose of light to alter conductivity across the membrane. As used herein, the terms "alter" and "change" may be used interchangeably. In some embodiments of the invention altering conductivity may include decreasing conductivity across a membrane as compared to conductivity across a normal or control membrane, and in certain embodiments of the invention altering conductivity may include increasing conductivity across a membrane as compared to conductivity across a normal, or control membrane.

In some embodiments of the invention, light-activated channels may be used to modify the transmembrane potential (and/or ionic composition) of cells (and/or their subcellular regions, and their local environment). For example, the use of inwardly rectifying cationic channels will depolarize cells by moving positively charged ions from the extracellular environment to the cytoplasm. Under certain conditions, their use can decrease the intracellular pH (and/or cation concentration) or increase the extracellular pH (and/or cation concentration). In some embodiments, the presence of light-activated ion channels of the invention in a membrane of one, two, three, or more (e.g. a plurality) of cells in a tissue or organism, can result in depolarization of the single cell or the plurality of cells by contacting the light-activated ion channels with light of suitable wavelength to activate the channel and increase conductivity of the membrane(s). The terms "conductance" and "conductivity" may be used interchangeably herein in reference to the movement of ions across a membrane.

CsChrimson Light-Activated Ion Channels

CsChrimson light-activated ion channels and variants thereof of the invention are transmembrane channel polypeptides that use light energy to open, permitting ion conductance through their pore across the membrane, thus altering the potential of the membrane in which they are expressed. Many ion channels do not express well in a cell and/or their expression may be toxic to the cell and reduce cell health. Thus, it was necessary to prepare and screen numerous channelrhodopsin light-activated ion channel polypeptides to identify the CsChrimson light-activated ion channels of the invention that can be expressed in cells without significantly reducing cell health and viability.

CsChrimson light-activated ion channels of the invention have been found to be suitable for expression and use in mammalian cells without need for any kind of chemical supplement, and in normal cellular environmental conditions and ionic concentrations. Light-activated ion channels of the invention have been found to differ from many previously identified channels in that the CsChrimson light-activated ion channels activate at wavelengths of light in a range of 365 nm to 735 nm, with an optimal activation from light ranging from 530 nm to 640 nm, and a peak optimal activation at a wavelength of 590 nm. In certain embodiments of the invention, CsChrimson can drive spikes at a wavelength up to 735 nm.

Non-limiting examples of ions that can be moved through a pore of the invention include sodium ions, potassium ions, calcium ions, protons, etc. Routine methods may be used to measure different ion currents for light-activated ion channels of the invention. Light-activated ion channels of the invention can be activated by sustained light and/or by light pulses and by permitting ion conductance upon activation, light-activated ion channels of the invention can depolarize cells and alter, (which may also be to herein as "change"), the voltage in cells and organelles in which they are expressed. A non-limiting example of a light-activated ion channel of the invention is CsChrimson having an amino acid sequence set forth herein as SEQ ID NO: 1, and functional variants thereof. As used herein, a "light-activated ion channel of the invention" means a CsChrimson light-activated ion channel or functional variant thereof.

Certain embodiments of the invention include nucleic acid sequences that encode a CsChrimson polypeptide or variant thereof and methods that utilize such nucleic acids. Certain embodiments of the invention include CsChrimson polypeptide or variant thereof and methods of its use. The CsChrimson nucleic acid sequences and amino acid sequences used in aspects and methods of the invention may be "isolated" sequences. As used herein, the term "isolated" used in reference to a polynucleotide, nucleic acid sequence, or polypeptide sequence, means a polynucleotide, nucleic acid sequence, or polypeptide sequence that is separate from its native environment and present in sufficient quantity to permit its identification or use. Thus, a nucleic acid or polypeptide sequence that makes up a CsChrimson light-activated ion channel nucleic acid or polypeptide (or variant thereof) that is present in a vector, in a cell, tissue, or organism, etc., may be considered to be an isolated sequence if it did not originate in that cell, tissue, or organism. As used herein the term "host" used in reference to a membrane, cell, or organism means a membrane, cell, or organism in which a CsChrimson light-activated ion channel or variant thereof of the invention is expressed. Examples of a host membrane, cell, tissue, or organism include, but are not limited to mammalian (including but not limited to non-human primate, human, dog, cat, horse, mouse, rat, etc.), insect (including but not limited to *Drosophila*, etc.), fish and avian membranes, cells, tissues, and organisms. As used herein, the term "heterologous" means a membrane, cell, tissue, or organism that is not a *Chlamydomonas* or *Chloromonas* cell, tissue, or organism. A CsChrimson light-activated ion channel polypeptide of the invention or its encoding nucleic acid (or variants thereof) may be present in a heterologous membrane, cell, tissue, or organism.

When expressed in a cell, CsChrimson light-activated ion channels of the invention can be activated by contacting the cell with light having a wavelength between 365 nm to 735 nm, between about 530 nm and 735 nm, between about 570 nm and 650 nm, and between 570 nm and 600 nm. In some embodiments of the invention, peak activation may occur upon contact with light having a wavelength between 580 and 600 nm and in certain embodiments of the invention, peak activation may occur upon contact with light having a wavelength of about 590 nm. With respect to wavelength ranges presented herein, the ranges include the endpoints as listed.

Contacting an excitable cell that includes a CsChrimson light-activated ion channel or functional variant thereof of the invention with a light in the activating range of wavelengths strongly depolarizes the cell. Exemplary wavelengths of light that may be used to depolarize a cell expressing a CsChrimson light-activated ion channel or variant thereof of the invention, include wavelengths from at least about 365 nm, 385 nm, 405 nm, 425 nm, 445 nm, 465 nm, 485 nm, 505 nm, 525 nm, 545 nm, 565 nm, 585 nm, 605 nm, 625 nm, 645 nm, 665 nm, 685 nm, 705 nm, 725 nm, and 735 nm, including all wavelengths therebetweeen. In some embodiments, a CsChrimson light-activated ion channel or a variant thereof, may have a peak wavelength sensitivity in of 590 nm, and may elicit spikes up to 735 nm.

In some embodiments of the invention, a CsChrimson light-activated ion channel or variant thereof can drive temporally precise spikes with 1-5 ms pulse width at 0.5 mW/mm$^2$ to >10 mW/mm$^2$ in neurons at its optimal wavelength in slice and in cell culture; and can stimulate at frequency up to 10 Hz reliably at its optimal wavelength. In some embodiments of the invention, a wavelength that activates a CsChrimson light-activated ion channel or a variant thereof, is between 530 nm and 735 nm.

CsChrimson light-activated ion channels or variants thereof, of the invention permit ion conductance and depolarization when contacted under suitable conditions with an appropriate wavelength of light. As will be understood by those in the art that the term: "depolarized" used in the context of cells means an upward change in the cell voltage. For example, in an excitable cell at a baseline voltage of about −65 mV, a positive change in voltage, e.g., up to 5, 10, 15, 20, 30, 40, or more millivolts (mV) is a depolarization of that cell. When the change in voltage is sufficient to reach the cell's spike initiation voltage threshold an action potential (e.g. a spike) results. When a cell is depolarized by activating a light-activated ion channel of the invention with an appropriate wavelength of light, the cell voltage becomes more positive than the baseline level, and an incoming signal may more easily raise the cell's voltage sufficiently to reach the threshold and trigger an action potential in the cell. It has been discovered that by contacting a cell expressing a CsChrimson light-activated ion channel or variant thereof of the invention with light in the range between about 365 nm to about 735 nm, the voltage of the cell becomes less negative and may rise by at least about 20, 30, 40, 50, 60, 70, 80, 90, 100, mV (depending on the cell type) thus, depolarizing the cell. As used herein, the term "activate" when used in reference to a light-activated ion channel of the invention, means to open the channel making it permissive to ion conduction through the channel.

Specific ranges of wavelengths of light that in some embodiments of the invention are useful to activate CsChrimson light-activated ion channels or variants thereof of the invention are provided and described herein. It will be understood that a light of appropriate wavelength for activation and will have a power and intensity appropriate for activation. It is well known in the art that light pulse duration, intensity, and power are parameters that can be altered when activating a channel with light. Thus, a skilled artisan will be able to adjust power, intensity appropriately when using a wavelength taught herein to activate a light-activated ion channel of the invention. A dose of light that contacts a CsChrimson light-activated ion channel or variant thereof of the invention may be determined based on the wavelength, pulse length, and power of the light that contacts the light-activated ion channel. Thus, as a non-limiting example, a dose may have a wavelength of 550 nm, a 4 ms pulse length, and a 0.5 mW/mm$^2$ power and another light dose may have a wavelength of 550 nm, a 3 ms pulse length and a 0.5 mW/mm$^2$ power. Those skilled in the art can utilize art-known methods to select a dose of light by independently selecting a wavelength, a pulse length, and a power for the light with which a light-activated ion channel of the invention is contacted. In some embodiments, wavelength and pulse length may be held steady, and power incrementally increased to examine activation parameters of a light-activated ion channel of the invention. Similarly, certain embodiments of the invention may include incremental wavelength increases while pulse length and power are held steady; or incremental pulse length increases while wavelength and power are held steady. In some embodiments of the invention two or more of wavelength, pulse length, and power of a light may be incrementally altered to examine the effect on activation of a light-activating ion channel of the invention.

A benefit of a light-activated ion channel of the invention is the ability to "tune" the light-activated ion channel's response using appropriate illumination variables (e.g., wavelength, intensity, duration, etc.), which are also referred to herein as "dose", to activate the channel. Methods of adjusting illumination variables are well known in the art and representative methods can be found in publications such as: Lin, J., et al., Biophys. J. 2009 Mar. 4; 96(5): 1803-14; Wang, H., et al., 2007 Proc Natl Acad Sci USA. 2007 May 8; 104(19): 8143-8. Epub 2007 May 1, each of which is incorporated herein by reference. Thus, it is possible to utilize a narrow range of one or more illumination characteristics to activate a light-activated ion channel of the invention.

CsChrimson light-activated ion channels and variants thereof of the invention can be used to depolarize excitable cells in which one or more light-activated ion channels of the invention are expressed. In some embodiments, a CsChrimson light-activated ion channel or a variant thereof, can be expressed in a sub-population of cells in a cell population that also includes one or more additional subpopulations of cells that express light-activated ion channels that are activated by wavelengths of light that do not activate a CsChrimson light-activated ion channel or a variant thereof of the invention. The expression of light-activated ion channels that are activated by different wavelengths of light in distinct, separate, subpopulations in a cell population can permit application of different illumination parameters to the population with an effect of differentially activating the different subpopulations through the use specific wavelengths of light, thus permitting controlled activation of a mixed population of light-activated channels.

Not all channelrhodopsins can be expressed in cells and utilized in this fashion, because many do not traffic properly and/or function in mammalian cells. Many channelrhodopsins and polypeptides comprising sequences derived therefrom were screened in order to identify CsChrimson as effectively functioning in mammalian cells. CsChrimson responds strongly to far red light, and therefore, because many other channelrhodopsins that depolarize cells respond strongly to ultraviolet or blue light, CsChrimson can be expressed in a separate population of cells from a population of cells expressing one of these other opsins, allowing multiple colors of light to be used to excite these two populations of cells or neuronal projections from one site, at different times. Other pairs of targets that could be modulated with two colors of light in the same illumination area include, but are not limited to two projections to/from one site, or combinations of the cell, its projections, and its organelles, given the ability to target the molecule sub-cellularly.

In some embodiments of the invention, light-activated channels are used to modify the transmembrane potential (and/or ionic composition) of cells (and/or their sub-cellular regions, and their local environment). In particular, the use of inwardly rectifying cationic channels will depolarize cells by moving positively charged ions from the extracellular environment to the cytoplasm. Under certain conditions, their use can decrease the intracellular pH (and/or cation concentration) or increase the extracellular pH (and/or cation concentration).

It has been identified that CsChrimson light-activated ion channels, and variants thereof of the invention are, in some embodiments of the invention, activated at different wavelengths than previously identified light-activated ion channels. Thus, light-activated ion channels of the invention can be used in either alone, using a selective light spectrum for activation and depolarization and can also be used in combination with other light-activated ion channels that utilize different wavelength of light for activation and depolarization, thus allowing two, three, four, or more different wavelengths of light to be used to depolarize different sets or subpopulations of cells in a tissue or organism by expressing channels with different activation spectra in different cells and then illuminating the tissue and/or organism with the appropriate wavelengths of light to activate the channels and depolarize the cells.

As described herein, CsChrimson light-activated ion channels or variants thereof of the invention can depolarize cells in strong response to light with sufficient spectral independence from that of other light-activate ion channels, thus allowing multiple colors of light to be used to depolarize different sets of cells in the same tissue, by expressing channels with different activation spectra genetically in different cells, and then illuminating the tissue with different colors of light in suitable dose to activate one type of light-activated ion channel but not the other type of light-activated ion channel.

In a non-limiting example of a combined expression strategy, a CsChrimson light-activated channel polypeptide can be expressed in a set of cells in a tissue and another light-activated channel polypeptide known as "Chronos" [see PCT Publication No. WO2013/071231 and Nature Methods (2014) volume 11(3) 338-346, published online Feb. 9, 2014] can be expressed in another set of cells in the tissue. Chronos has photocurrent generation at all illumination wavelengths except for red wavelength illumination. Chronos can depolarize cells in response to <5 ms pulse of 50-100 $\mu W$ $mm^{-2}$ of blue or green light with sufficient spectral independence from CsChrimson. Illuminating the tissue with 630 nm light preferentially depolarizes the first set of cells, and illuminating the tissue with 470 nm light at low powers (<5 mW $mm^{-2}$) preferentially depolarizes the second set of cells, thus permitting multiple colors of light to be used to depolarize different sets of cells in the same tissue.

Taxonomy and Sequence Sources

In particular, the present invention includes, in part, novel light-activated ion channels, their expression in cells, and their use to depolarize cells. The amino acid sequence of a CsChrimson light-activated ion channel polypeptide of the invention comprises an amino acid sequence derived from the sequence of a *Chlamydomonas* rhodopsin polypeptide and an amino acid sequence derived from the sequence of a *Chloromonas* rhodopsin polypeptide. Residues 1-79 of the CsChrimson sequence set forth herein as SEQ ID NO: 1 are in a non-transmembrane region of the CsChrimson light-activated ion channel polypeptide. Residues 80-315 of the CsChrimson sequence set forth herein as SEQ ID NO: 1 are in a putative transmembrane region of the CsChrimson light-activated ion channel polypeptide.

Variant CsChrimson Light-Activated Ion Channel Sequences

Light-activated ion channel molecules of the invention include CsChrimson molecules and may also include variants of the CsChrimson polypeptide set forth herein as SEQ ID NO: 1, and variants of the nucleic acid set forth herein as SEQ ID NO: 13, which encodes the CsChrimson polypeptide set forth as SEQ ID NO: 1. A non-limiting example of a variant of CsChrimson is the light-activated ion channel polypeptide comprising the amino acid sequence set forth herein as SEQ ID NO: 16, which is encoded by the nucleic acid sequence set forth herein as SEQ ID NO: 17. This CsChrimson light-activated ion channel variant polypeptide includes a K→R substitution at position 171 of the CsChrimson polypeptide sequence set forth herein as SEQ ID NO: 1.

Additional non-limiting examples of CsChrimson light-activated ion channel variant polypeptides are polypeptides variants that include one or more amino acid substitutions, and 1, 2, 3, 4, or 5 of the substitutions correspond to E127A, E127D, E127N, E127P, E127Q, E160A, K242A, F139S, T149G, T149N, or T149S substitutions in the sequence set forth as SEQ ID NO: 1.

In some embodiments of the invention, the amino acid sequence of the non-transmembrane region of a CsChrimson light-activated ion channel polypeptide variant may have at least 80%, 85%, 90%, 95%, 96%, 97%, 98%, 99% or 100% identity to the non-transmembrane region of the sequence of CsChrimson set forth as SEQ ID NO: 1. In certain embodiments of the invention, the amino acid sequence of the transmembrane region of a CsChrimson light-activated ion channel polypeptide variant may have at least 60%, 65% 70%, 75%, 80%, 85%, 90%, 95%, 96%, 97%, 98%, 99%, or 100%, identity to the putative transmembrane region of the sequence of CsChrimson set forth herein as SEQ ID NO: 1. Thus, the amino acid sequence of the non-transmembrane region of a variant CsChrimson polypeptide may be more constrained than the amino acid sequence of the putative transmembrane region with respect to the extent of permissible modifications from the amino acid sequence of CsChrimson (SEQ ID NO: 1) in order to permit the CsChrimson variant to have all, or at least a portion of the level of function of CsChrimson when contacted with light under suitable conditions to activate the channel. In some aspects of the invention, a CsChrimson variant has at least 10%, 20%, 30%, 40%, 50%, 60%, 70%, 80%, 90%, 100% of the level of light-activated function of the CsChrimson light-activated ion channel from which the variant was derived.

As used herein, the term "identity" refers to the degree of relatedness or similarity between two or more polypeptide sequences (or nucleic acid sequences), which may be determined by the alignment and match between the sequences. The percentage is obtained as the percentage of identical amino acids in two or more sequences taking account of gaps and other sequence features. The identity between polypeptide sequences can be determined by means of art-known procedures. Algorithms and programs are available and routinely used by those in the art to determine identity between polypeptide sequences and to determine identity between nucleic acid sequences. Non-limiting examples of programs and algorithms include BLASTP, BLASTN and FASTA (Altschul et al., NCB NLM NIH Bethesda Md. 20894; Altschul et al., 1990), Online BLAST programs from the National Library of Medicine are available, for example, at blast.ncbi.nlm.nih.gov/Blast.cgi.

CsChrimson light-activated ion channel variants can be identified based on sequence similarity to the sequence of the CsChrimson light-activated ion channel, which is set forth as SEQ ID NO: 1. Based on the teaching provided herein regarding the CsChrimson sequence having light-activated ion channel function and activity, additional sequences (referred to as CsChrimson variants) with sufficient amino acid sequence similarity/identity to a CsChrimson sequence, can be identified. The presence of functionality, e.g., activation of a channel by contact with suitable light can be determined using methods described herein, and functional variants of a CsChrimson light-activated ion channel of the invention can be used in methods described herein. It is understood that that the level of sequence identity with a light-activated ion channel of the invention plus functionality with respect to activation by suitable light contact can be characteristics used to identify additional light-activated ion channels using standard procedures for sequence alignment, comparisons, and assays for ion channel activity.

A variant of a CsChrimson light-activated ion channel of the invention may comprise a CsChrimson polypeptide sequence (and be encoded by a nucleic acid sequence) with one or more sequence modifications. As used herein the term "modified" or "modification" in reference to a polypeptide sequence refers to a change such one or more of an insertion, deletion, or substitution of 1, 2, 3, 4, 5, 6, 7, 8, 9, 10, or more amino acids in the sequence as compared to the CsChrimson sequence set forth herein as SEQ ID NO: 1. As an example, though not intended to be limiting, a modified polypeptide sequence is identical to the amino acid sequence set forth as SEQ ID NO: 1 except that it has one or more amino acid substitutions, deletions, insertions, or combinations thereof. In some embodiments of the invention a variant CsChrimson sequence may include of 1, 2, 3, 4, 5, 6, 7, 8, 9, 10, or more amino acid substitutions in a CsChrimson light-activated ion channel polypeptide sequence of the invention.

The sequence of the CsChrimson light-activated ion channel polypeptide provided herein can be modified with one or more substitutions, deletions, insertions, or other modifications and the resulting CsChrimson light-activated ion channel variant can be tested using methods described herein for characteristics including, but not limited to: expression, cell localization, activation and depolarization in response to contact with light using methods disclosed herein. Exemplary modifications include, but are not limited to conservative amino acid substitutions, which will produce molecules having functional characteristics similar to those of the molecule from which such modifications are made. Conservative amino acid substitutions are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution because both are similarly sized, negatively charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). CsChrimson light-activated ion channel variants that include modifications, such as, but not limited to one, two, three, four, or more conservative amino acid substitutions can be identified and tested for characteristics including, but not limited to: expression, cell localization, activation and depolarization and depolarization effects in response to contact with light using methods disclosed herein.

As described elsewhere herein, the transmembrane region of a CsChrimson light-activated ion channel variant of the invention may include modifications that result in an amino acid sequence having at least 60%, 70%, 80%, 85%, 90%, 95%, 96%, 97%, 98%, 99%, or 100% identity with the putative transmembrane region in the sequence set forth as SEQ ID NO: 1, and modifications that result in an amino acid sequence having at least 85%, 90%, 95%, 96%, 97%, 98%, 99%, or 100% identity with the non-transmembrane region in the sequence set forth as SEQ ID NO: 1. Sequence identity can be determined using standard techniques known in the art.

Variant CsChrimson light-activated ion channel polypeptides of the invention may be shorter or longer than the CsChrimson light-activated ion channel polypeptide sequence set forth herein as SEQ ID NO: 1. Thus, a light-activated ion channel polypeptide may be a full-length polypeptide or functional fragment thereof. In addition, nucleic acids of the invention may be used to obtain additional coding regions, and thus additional polypeptide sequences, using techniques known in the art.

In some aspects of the invention, the amino acid sequence of a CsChrimson light-activated ion channel polypeptide variant may have at least 80%, 81%, 82%, 83%, 84%, 85%, 86%, 87%, 88%, 89%, 90%, 91%, 92%, 93%, 94%, 95%, 96%, 97%, 98%, or 99% overall identity with the amino acid sequence of CsChrimson set forth herein as SEQ ID NO: 1. Art-known alignment methods and tools can be used to align substantially similar sequences permitting positional identification of amino acids that may be modified as described herein to prepare a variant CsChrimson light-activated ion channel of the invention. Standard sequence analysis tools and computer programs, such as those used for alignment, etc. can be used to identify variant CsChrimson light-activated ion channels of the invention that share one or more functional properties with the CsChrimson light-activated ion channel described herein.

Sequence modifications such as substitutions, insertions, or deletions may be prepared by site specific mutagenesis of nucleic acids in the DNA encoding a CsChrimson light-activated ion channel polypeptide, using cassette or PCR mutagenesis or other techniques known in the art, to produce DNA encoding the variant CsChrimson light-activated ion channel, and thereafter expressing the DNA in recombinant cell culture. Amino acid sequence variants are characterized by the predetermined nature of the variation, a feature that sets them apart from naturally occurring allelic or interspecies variation of the light-activated ion channels of the invention. Variant CsChrimson light-activated ion channels generally exhibit the same qualitative biological activity as a CsChrimson light-activated ion channel, although variants can also be selected that have modified characteristics.

A site or region for introducing an amino acid sequence modification may be predetermined, and the mutation per se need not be predetermined. For example, to optimize the performance of a mutation at a given site, random mutagenesis may be conducted at the target codon or region and the expressed variant CsChrimson light-activated ion channel screened for the optimal combination of desired activity. Techniques for making substitution mutations at predetermined sites in DNA having a known sequence are well known, for example, M13 primer mutagenesis and PCR mutagenesis.

Amino acid substitutions are typically of single residues; and insertions usually will be on the order of from about 1 to 20 amino acids, although larger insertions may be tolerated. Deletions may range from about 1 to about 20 residues, although in some cases deletions may be larger. Substitutions, deletions, insertions or any combination thereof may be used to arrive at a CsChrimson light-activated ion channel variant of the invention. Generally these changes may be done on a few amino acids to minimize the alteration of the molecule. However, larger changes may be tolerated in certain circumstances.

CsChrimson light-activated ion channel variants may exhibit the same qualitative light-activated ion channel activity as the CsChrimson polypeptide set forth herein as SEQ ID NO: 1, but may show some altered characteristics such as altered photocurrent, stability, speed, compatibility, and toxicity, or a combination thereof. For example, the polypeptide can be modified such that it has an increased photocurrent and/or has less toxicity than another light-activated ion channel polypeptide.

A CsChrimson light-activated ion channel polypeptide variant of the invention can incorporate unnatural amino acids as well as natural amino acids. An unnatural amino acid can be included in a light-activated ion channel of the invention to enhance a characteristic such as photocurrent, stability, speed, compatibility, or to lower toxicity, etc.

According to principles of this invention, the performance of CsChrimson light-activated ion channel molecules or variants thereof can be tuned for optimal use, including in the context of their use in conjunction with other molecules or optical apparatus. For example, in order to achieve optimal contrast for multiple-color stimulation, one may desire to either improve or decrease the performance of one molecule with respect to one another, by the appendage of trafficking enhancing sequences (non-limiting examples of which include ER2, KGC, etc.) or creation of genetic variants by site-directed mutagenesis, directed evolution, gene shuffling, or altering codon usage. CsChrimson light-activated ion channel molecules, or variants thereof, may have inherently varying spectral sensitivity. This may be used to advantage in vivo (where scattering and absorption will vary with respect to wavelength, coherence, and polarization), by tuning the linearity or non-linearity of response to optical illumination with respect to time, power, and illumination history.

In some embodiments, the invention includes the use of targeted site-directed mutagenesis at specific amino acid residues of CsChrimson polypeptides, or variants thereof. Specific locations for single mutations can be identified and alone, or in combination with two or more additional mutations can be placed into a CsChrimson sequence, or a variant thereof, and tested with respect to their activation and photocurrent amplitude. Thus, sequences of CsChrimson light-activated ion channels, or variants thereof, of the invention can be modified and the resulting polypeptides tested using methods disclosed herein.

Another aspect of the invention provides nucleic acid sequences that code for a CsChrimson light-activated ion channel of the invention, or variants thereof. It would be understood by a person of skill in the art that CsChrimson light-activated ion channel polypeptides of the present invention, or variants thereof, can be coded for by various nucleic acids. Each amino acid in the protein is represented by one or more sets of 3 nucleic acids (codons). Because many amino acids are represented by more than one codon, there is not a unique nucleic acid sequence that codes for a given protein. It is well understood by those of skill in the art how to make a nucleic acid that can code for light-activated ion channel polypeptides of the invention by knowing the amino acid sequence of the protein. A nucleic acid sequence that codes for a polypeptide or protein is the "gene" of that polypeptide or protein. A gene can be RNA, DNA, or other nucleic acid than will code for the polypeptide or protein.

It is understood in the art that the codon systems in different organisms can be slightly different, and that therefore where the expression of a given protein from a given organism is desired, the nucleic acid sequence can be modified for expression within that organism. Thus, in some embodiments, a CsChrimson light-activated ion channel polypeptide, or variant thereof, of the invention is encoded by a mammalian-codon-optimized nucleic acid sequence, which may in some embodiments be a human-codon optimized nucleic acid sequence. An aspect of the invention provides a nucleic acid sequence that codes for a CsChrimson light-activated ion channel, or variant thereof, that is optimized for expression with a mammalian cell. In some embodiments of the invention, a nucleic acid that encodes a CsChrimson light-activated ion channel, or variant thereof, of the invention includes a nucleic acid sequence optimized for expression in a human cell.

Delivery of CsChrimson Light-Activated Ion Channels and Variants Thereof

Delivery of a CsChrimson light-activated ion channel polypeptide or variant thereof, to a cell and/or expression of a CsChrimson light-activated ion channel or variant thereof, in a cell can be done using art-known delivery means. (see, for example Chow et al. Nature 2010 Jan. 7; 463(7277): 98-102.)

In some embodiments of the invention a light-activated ion channel polypeptide of the invention is included in a fusion protein. It is well known in the art how to prepare and utilize fusion proteins that comprise a polypeptide sequence. In certain embodiments of the invention, a fusion protein can be used to deliver a CsChrimson light-activated ion channel, or variant thereof, to a cell and can also in some embodiments be used to target a CsChrimson light-activated ion channel, or variant thereof, of the invention to specific cells or to specific cells, tissues, or regions in a subject. Targeting and suitable targeting sequences for delivery to a desired cell, tissue or region can be performed using art-known procedures.

It is an aspect of the invention to provide a CsChrimson light-activated ion channel polypeptide or variant thereof of the invention that is non-toxic, or substantially non-toxic in cells in which it is expressed. In the absence of light, a light-activated ion channel of the invention does not significantly alter cell health or ongoing electrical activity in the cell in which it is expressed.

In some embodiments of the invention, a CsChrimson light-activated ion channel, or variant thereof, of the invention is genetically introduced into a cellular membrane, and reagents and methods are provided for genetically targeted expression of light-activated ion channel polypeptides, including CsChrimson and variants thereof. Genetic targeting can be used to deliver light-activated ion channel polypeptides of the invention to specific cell types, to specific cell subtypes, to specific spatial regions within an organism, and to sub-cellular regions within a cell. Genetic targeting also relates to the control of the amount of a CsChrimson light-activated ion channel polypeptide, or variant thereof, that is expressed, and the timing of the expression.

Some embodiments of the invention include a reagent for genetically targeted expression of a CsChrimson light-activated ion channel polypeptide or variant thereof, wherein the reagent comprises a vector that contains the gene for the CsChrimson light-activated ion channel polypeptide or variant thereof.

As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert CsChrimson light-activated ion channel polypeptides, and variants thereof, into dividing and non-dividing cells and can insert CsChrimson light-activated ion channel polypeptides and variants thereof to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein.

In certain embodiments of the invention, a vector may be a lentivirus comprising the gene for a CsChrimson light-activated ion channel of the invention, or variant thereof. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a CsChrimson light-activated ion channel polypeptide or variant thereof in a wide variety of cell types—thus a promoter for a gene that is widely expressed in a variety of cell types, for example a "housekeeping gene" can be used to express a CsChrimson light-activated ion channel polypeptide, or variant thereof, in a variety of cell types. Non-limiting examples of general promoters are provided elsewhere herein and suitable alternative promoters are well known in the art.

In certain embodiments of the invention, a promoter may be an inducible promoter, examples of which include, but are not limited to tetracycline-on or tetracycline-off, or tamoxifen-inducible Cre-ER.

Methods of Use of CsChrimson Light Activated Ion Channels and Variants Thereof

CsChrimson light activated ion channels, and variants thereof of the invention are well suited for targeting cells and specifically altering voltage-associated cell activities. In some embodiments of the invention, light-activated ion channels of the invention can be utilized to introduce cations into cells, thus activating endogenous signaling pathways (such as calcium dependent signaling), and then drugs can be applied that modulate the response of the cell (using a calcium or voltage-sensitive dye). This allows drug screening using just light to activate the channels of interest, and using just light to read out the effects of a drug on the channels of interest.

CsChrimson can be activated by far-red light, and thus allows excitation of cells with a color of light heretofore not generally used in biotechnology for excitation of cells. By using for example, CsChrimson and Chronos [see PCT Publication No. WO2013/071231 and Nature Methods (2014) volume 11(3) 338-346, published online Feb. 9, 2014 for details on Chronos] together, excitation of two different populations of cells in the same tissue or in the same culture dish can be performed. This type of simultaneous, two-color excitation is particularly promising for complex tissues such as the brain.

The performance of the above-described molecules can be tuned for optimal use, particularly in context of their use in conjunction with other molecules or optical apparatus. Such tuning can be done using standard methods known in the art. For example, in order to achieve optimal contrast for multiple-color stimulation, one may desire to either improve or decrease the performance of one molecule with respect to one another, by the appendage of trafficking enhancing sequences or creation of genetic variants by site-directed mutagenesis, directed evolution, gene shuffling, or altering codon usage. Molecules or classes of molecules may have inherently varying spectral sensitivity that may be functionally advantageous in vivo (where scattering and absorption will vary with respect to wavelength, coherence, and polarization), by tuning the linearity or non-linearity of response to optical illumination with respect to time, power, and illumination history.

Another aspect of the invention includes methods of using CsChrimson light-activated channels and variants thereof in cells in order to decrease the pH of the cell. Such a technique may be used to treat alkalosis in a cell, tissue, or subject.

Another aspect of the invention may involve methods of using light-activated proton pumps in conjunction with one or more CsChrimson light-activated ion channels or variants thereof in a cell for the coupled effect of hyperpolarization and intracellular alkalinization. For example, both phenomena can induce spontaneous spiking in neurons by triggering hyperpolarization-induced cation currents or pH-dependent hyper-excitability. Yet another aspect of the invention may include use of CsChrimson light-activated ion channels (or variants thereof) in cells to generate sub-cellular voltage or pH gradients, particularly at synapses and in synaptic vesicles to alter synaptic transmission, and in mitochondria to improve ATP synthesis in a cell, tissue, or subject.

Another aspect of the invention is the use CsChrimson light-activated ion channels or variants thereof of the invention with far-red (for example, 660, 700, 735 nm) light to perform non-invasive transcranial and/or transdural stimulation to modulate neural circuits.

Another aspect of the invention is the various compositions of matter that have now been reduced to practice, for example: plasmids encoding for the above genes have been prepared; lentiviruses carrying payloads encoding for the above genes have been prepared; adeno-associated viruses carrying payloads encoding for the above genes have been prepared; cells expressing the above genes have been prepared. *Drosphila* expressing CsChrimson have been prepared.

Working operation of a prototype of this invention was demonstrated by genetically expressing CsChrimson light-activated ion channel molecules of the invention in excitable cells, illuminating the cells with suitable wavelengths of light, and demonstrating rapid depolarization of the cells in response to the light, as well as rapid release from depolarization upon cessation of light. Depending on the particular implementation, methods of the invention allow light control of cellular functions in vivo, ex vivo, and in vitro.

In non-limiting examples of methods of the invention, CsChrimson light-activated ion channels and variants thereof of the invention are used in mammalian cells without need for any kind of chemical supplement, and in normal cellular environmental conditions and ionic concentrations. For example, genes encoding CsChrimson light-activated ion channels, and variants thereof, have been used in exemplary implementations of the invention. These sequences in humanized or mouse-optimized form allow depolarization at wavelengths described herein.

Cells and Subjects

Some aspects of the invention include cells used in conjunction with CsChrimson-encoding-nucleic acids and CsChrimson polypeptides (and variants thereof). A cell in which a CsChrimson light-activated ion channel or variant thereof of the invention may be expressed and may be used in methods of the invention include prokaryotic and eukaryotic cells. In certain embodiments of the invention, useful cells may be mammalian cells; including but not limited to cells of humans, non-human primates, dogs, cats, horses, rodents, etc. In some embodiments of the invention, useful cells may be non-mammalian cells; including but not limited to insect cells, avian cells, fish cells, plant cells, etc. Examples of cells in which a CsChrimson light-activated ion channel or variant thereof of the invention may be expressed are non-excitable cells and excitable cells, the latter of which includes cells able to produce and respond to electrical signals. Examples of excitable cell types include, but are not limited to, neurons, muscles, cardiac cells, and secretory cells (such as pancreatic cells, adrenal medulla cells, pituitary cells, etc.).

Non-limiting examples of cells that may be used in methods of the invention include: neuronal cells, nervous system cells, cardiac cells, circulatory system cells, visual system cells, auditory system cells, secretory cells, endocrine cells, or muscle cells. In some embodiments, a cell used in conjunction with methods and ion channels of the invention may be a healthy normal cell, which is not known to have a disease, disorder or abnormal condition. In some embodiments, a cell used in conjunction with methods and ion channels of the invention may be an abnormal cell, for example, a cell that has been diagnosed as having a disorder, disease, or condition, including, but not limited to a degenerative cell, a neurological disease-bearing cell, a cell model of a disease or condition, an injured cell, etc. In some embodiments of the invention, a cell may be a control cell.

Light-activated ion channels of the invention may be expressed in cells from culture, cells in solution, cells obtained from subjects, and/or cells in a subject (in vivo cells). Light-activated ion channels may be expressed and activated in cultured cells, cultured tissues (e.g., brain slice preparations, etc.), and in living subjects, etc. As used herein, a the term "subject" may refer to a human, non-human primate, cow, horse, pig, sheep, goat, dog, cat, bird, rodent, insect, or other vertebrate or invertebrate organism. In certain embodiments, a subject is a mammal and in certain embodiments a subject is a human.

Controls and Candidate Compound Testing and Drug Screening

CsChrimson light-activated ion channels and variants thereof of the invention and methods using CsChrimson light-activated ion channels and variants thereof of the invention can be utilized to assess changes in cells, tissues, and subjects in which they are expressed. Some embodiments of the invention include use of CsChrimson light-activated ion channels and variants thereof of the invention to identify effects of candidate compounds on cells, tissues, and subjects. Results of testing a CsChrimson light-activated ion channel or variant thereof of the invention can be advantageously compared to a control. In some embodiments of the invention one or more CsChrimson light-activated ion channels or variant thereof of the invention, may be expressed in a cell population and used to test the effect of candidate compounds on the cells. A "test" cell, membrane, tissue, or organism may be a cell, tissue, or organism in which activity of a light-activated ion channel of the invention may be tested or assayed. Results obtained using assays and tests of a test cell, membrane, tissue, or organism may be compared results obtained from the assays and tests performed in other test cells, membranes, tissues or organisms or assays and tests performed in control cells, membranes, tissues, or organisms.

As used herein a control value may be a predetermined value, which can take a variety of forms. It can be a single cut-off value, such as a median or mean. It can be established based upon comparative groups, such as cells or tissues that include the CsChrimson light-activated ion channel or variant thereof and are contacted with light, but are not contacted with a candidate compound and the same type of cells or tissues that under the same testing condition are contacted with the candidate compound. Another example of comparative groups may include cells or tissues that have a disorder, disease, or condition and groups without the disorder, disease, or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention.

As a non-limiting example of use of a CsChrimson light-activated ion channel or variant thereof to identify a candidate therapeutic agent or compound, a CsChrimson light-activated ion channel or variant thereof of the invention may be expressed in an excitable cell in culture or in a subject and the excitable cell may be contacted with a light that activates the CsChrimson light-activated ion channel or variant thereof and with a candidate therapeutic compound. In one embodiment, a test cell that includes a CsChrimson light-activated ion channel or variant thereof of the invention can be contacted with a light that depolarizes the cell and also contacted with a candidate compound. A control cell in such an example may be a cell that includes the CsChrimson light-activated ion channel or variant thereof that is not contacted with the activating light and/or the candidate compound). The cell, tissue, and/or subject that include the cell can be monitored for the presence or absence of a change that occurs in the test conditions versus the control conditions. For example, in a cell, a change may be a change in the depolarization or in a depolarization-mediated cell characteristic in the test cell versus a control cell, and a change in depolarization or the depolarization-mediated cell characteristic in the test cell compared to the control may indicate that the candidate compound has an effect on the test cell or tissue that includes the cell. In some embodiments of the invention, a depolarization-mediated cell characteristic may be a an action potential, pH change in a cell, release of a neurotransmitter, etc. and may in come embodiments, include a downstream effect on one or more additional cells, which occurs due to the depolarization of the cell that includes the CsChrimson light-activated ion channel, or variant thereof. Art-known methods can be used to assess depolarization and depolarization-mediated cell characteristics and changes to the depolarization or depolarization-mediated cell characteristics upon activation of a CsChrimson light-activated ion channel or variant thereof of the invention, with or without additional contact with a candidate compound.

Candidate-compound identification methods of the invention that are performed in a subject, may include expressing a CsChrimson light-activated ion channel or variant thereof in a subject, contacting the subject with a light under suitable conditions to activate the light-activated ion channel and depolarize the cell, and administering to the subject a candidate compound. The subject is then monitored to determine whether any change occurs that differs from a control effect in a subject. In addition, for example, a cell in culture can be contacted with a light appropriate to activate a CsChrimson light-activated ion channel or variant thereof of the invention in the presence of a candidate compound. A result of such contact with the candidate compound can be measured and compared to a control value as a determination of the presence or absence of an effect of the candidate compound on the cell.

Methods of identifying effects of candidate compounds using CsChrimson light-activated ion channels, and variants thereof, of the invention may also include additional steps and assays to further characterizing an identified change in the cell, tissue, or subject when the cell is contacted with the candidate compound.

In a non-limiting example of a candidate drug identification method of the invention, cells that include a CsChrimson light-activated ion channel, or variant thereof of the invention are depolarized, thus triggering release of a neurotransmitter from the cell, and then drugs are applied that modulate the response of the cell to depolarization (determined for example using patch clamping methods or other suitable art-known means). Such methods enable drug screening using light to activate the channels of interest, and using light to read out the effects of a drug on the channels and channel-containing cells of interest.

In some embodiments, CsChrimson light-activated ion channel polypeptides, and variants thereof, of the invention can be used in test systems and assays for assessing membrane protein trafficking and physiological function in heterologously expressed systems and the use of use of light-activated channels to depolarize a cell.

In some embodiments of the invention, testing in a cell, tissue, or subject can also include one or more cells that has a CsChrimson light-activated ion channel or variant thereof of the invention, and that also has one, two, three, four or more additional different light-activated ion channels, wherein at least one, two, three, four or more of the additional light-activated ion channels is activated by contact with light having a different wavelength than used to activate the CsChrimson light-activated ion channel, or variant thereof of the invention. Thus, in some aspects of the invention, two-color assays (or assays utilizing 3, 4, 5, or more wavelength colors) can be performed. For example, Chronos (for blue light activation) and CsChrimson (for red light activation) can be expressed in separate sets cells that represent non-overlapping neuronal populations. Following expression, the cell population can be exposed to light and the wavelength and timing and "dose" of light can be optimized. As used herein the term "dose" in reference to light, may take into account of wavelength, pulse length, intensity, of the light with which a light-activated ion channel of the invention is contacted.

It will be understood that combinations of 2, 3, 4, or more light-activated ion channels may be expressed in separate subpopulations of a population of cells and then exposed to doses of light in a manner as described here to optimize their use in assays and treatments of the invention. A non-limiting example of a process to prepare and use a multi-light activated population of cells is as follows. A first light-activated ion channel is expressed in a first subpopulation of a population of cells; a second light-activated ion channel is expressed in a second subpopulation of the population of cells, wherein the first and second subpopulations are non-overlapping subpopulations, and the first light-activated ion channel and second light activated ion channel are have ranges of activating light wavelengths that do not entirely overlap. The population of cells is contacted with a plurality of first light test doses comprising combinations of wavelength, pulse width, and power that activate the first subpopulation, and the transmembrane voltage deflection is measured in a cell of the second subpopulation of cells contacted with the first light test doses. The first light test dose that includes a maximum light power that activates the light activated ion channel in first subpopulation of cells and results in a minimum sub-threshold transmembrane voltage deflection in the second subpopulation of cells is determined. The population of cells is then contacted with a plurality of first light test doses comprising a lower power than the maximum first light power that was determined, and a first light test doses that activate the first light activated ion channel (at the lower powers) are determined. The population of cells is then contacted with a plurality of second light test doses that include combinations of light wavelength, pulse width, and power that activate the second subpopulation, and a second light test dose comprising a second light power that activates the second subpopulation of cells is determined. Assays can be performed using such a population of cells, that includes contacting the population of cells with the first light test dose and the second light test dose determined using the steps above. The above-described process of optimizing light dose parameters for multi-light activated ion channels can be used to design and implement assays that include light-activated ion channels of the invention, as well as other light-activated ion channels that are known in the art.

A non-limiting example of a procedure for optimizing the use of two-color activated populations of cells is provided as follows. A population that has Chronos and CsChrimson expressed in different sub-populations is contacted with blue light having a wavelength between 400 nm and 500 nm, or between 450 nm to 500 nm, and having a pulse width of between 1 and 5 ms for activation. A pulse width of 5 ms provides for minimum sub-threshold crosstalk in the blue light, which is defined as <15 mV, <10 mV, and optimally as <5 mV. The maximum blue light power that can be used is determined using by patch clamping CsChrimson-expressing cells, illuminating with blue light and measuring voltage deflection. Optimally using blue light power such that maximum voltage deflection is <10mV, which in some embodiments may be 0.4 to 0.6 mW/mm$^2$. The optimal blue light power that can be used to drive Chronos is determined using the same conditions as above, except using lower light power, such as 50 µW/mm$^2$ to 0.4 mW/mm$^2$, which in some embodiments may be 0.2 mW/mm$^2$. Power depends on expression system and cell type used to prepare the population. The population can be contacted with red light having a wavelength, for example, of between 600 nm and 735 nm, 620 nm and 640 nm, or 570 nm and 650 nm, and with a pulse width of between 1 and 5 ms for activation, which in some embodiments may be optimized at 5 ms. In certain embodiments of the invention, the optimal light power to drive CsChrimson in the red may be determined by ramping light powers from for example, 0.1 mW/mm$^2$ to 100 mW/mm$^2$, or from 0.5 mW/mm$^2$ to 10 mW/mm$^2$. The method may be optimized such that a minimum red light power is used to achieve 100% spiking for CsChrimson.

Methods of Treatment Using CsChrimson or Variant Thereof

Some aspects of the invention include methods of treating a disorder, disease, or condition in a cell, tissue, or subject using CsChrimson light-activated ion channels, or variants thereof, of the invention. Treatment methods of the invention may include administering to a subject in need of such treatment, a therapeutically effective amount of a CsChrimson light-activated ion channel, or variant thereof, of the invention to treat the disorder, disease, or condition. It will be understood that a treatment may be a prophylactic treatment or may be a treatment administered following the diagnosis of a disease or condition. A treatment of the invention may reduce or eliminate a symptom or characteristic of a disorder, disease, or condition or may eliminate the disorder, disease, or condition itself. It will be understood that a treatment of the invention may reduce or eliminate progression of a disease, disorder or condition and may in some instances result in the regression of the disease, disorder, or condition. A treatment need not entirely eliminate the disease, disorder, or condition to be effective. In some embodiments of the invention one or more CsChrimson light-activated ion channels, or variants, of the invention may be expressed in a cell population and used in methods to treat a disorder, disease, or condition.

Administration of a CsChrimson light-activated ion channel or variant thereof, of the invention may include administration of a pharmaceutical composition that includes a cell, wherein the cell expresses the CsChrimson light-activated ion channel, or variant thereof. Administration of a CsChrimson light-activated ion channel or variant thereof, of the invention may include administration of a pharmaceutical composition that includes a vector, wherein the vector comprises a nucleic acid sequence encoding the CsChrimson light-activated ion channel or variant thereof, and the administration of the vector results in expression of the CsChrimson light-activated ion channel, or variant thereof in a cell in the subject.

An effective amount of a CsChrimson light-activated ion channel or variant thereof, is an amount that increases the level of the CsChrimson light-activated ion channel or variant thereof, in a cell, tissue, or subject to a level that is beneficial for the subject. An effective amount may also be determined by assessing physiological effects of administration on a cell or subject, such as a decrease in symptoms following administration. Other assays will be known to those skilled in the art and can be employed for measuring the level of the response to a treatment. The amount of a treatment may be varied for example by increasing or decreasing the amount of the CsChrimson light-activated ion channel or variant thereof that is administered, by changing the therapeutic composition in which the light-activated ion channel is administered, by changing the route of administration, by changing the dosage timing, by changing the activation amounts and parameters of a light-activated ion channel of the invention, and so on. The effective amount will vary with the particular condition being treated, the age and physical condition of the subject being treated; the severity of the condition, the duration of the treatment, the nature of the concurrent therapy (if any), the specific route of administration, and the like factors within the knowledge and expertise of the health practitioner. For example, an effective amount may depend upon the location and number of cells in the subject in which the light-activated ion channel is to be expressed. An effective amount may also depend on the location of the tissue to be treated.

Effective amounts will also depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. In general, for therapeutic use, a maximum dose of a composition to increase the level of a CsChrimson light-activated ion channel or variant thereof, and/or to alter the length or timing of activation of a CsChrimson light-activated ion channel or variant thereof in a subject (alone or in combination with other therapeutic agents) may be used, that is the highest safe dose or amount according to sound medical judgment. It will be understood by those of ordinary skill in the art, however, that a health-care provider or patient may insist upon a lower dose or tolerable dose for medical reasons, psychological reasons or for virtually any other reasons.

A CsChrimson light-activated ion channel or variant thereof of the invention may be administered using art-known methods. In some embodiments a nucleic acid that encodes a light-activated ion channel polypeptide of the invention is administered to a subject and in certain embodiments a light-activated ion channel polypeptide is administered to a subject. The manner and dosage administered may be adjusted by the individual physician or veterinarian, particularly in the event of any complication. The absolute amount administered will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compositions that deliver CsChrimson light-activated ion channels or variants thereof of the invention may be administered alone, in combination with each other, and/or in combination with other drug therapies, or other treatment regimens that are administered to subjects. A pharmaceutical composition used in the foregoing methods preferably contain an effective amount of a therapeutic compound that will increase the level of a CsChrimson light-activated ion channel polypeptide or variant thereof to a level that produces the desired response in a unit of weight or volume suitable for administration to a subject.

The dose of a pharmaceutical composition that is administered to a subject to increase the level of the CsChrimson light-activated ion channel or variant thereof in cells of the subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The amount and timing of activation of a light-activated ion channel of the invention (e.g., light wavelength, length of light contact, etc.) that has been administered to a subject can also be adjusted based on efficacy of the treatment in a particular subject. Parameters for illumination and activation of light-activated ion channels that have been administered to a subject can be determined using art-known methods and without requiring undue experimentation.

Various modes of administration will be known to one of ordinary skill in the art that can be used to effectively deliver a pharmaceutical composition to increase the level of a CsChrimson light-activated ion channel or variant thereof of the invention in a desired cell, tissue or body region of a subject. Methods for administering such a composition or other pharmaceutical compound of the invention may be topical, intravenous, oral, intracavity, intrathecal, intrasynovial, buccal, sublingual, intranasal, transdermal, intravitreal, subcutaneous, intramuscular, and/or intradermal administration. The invention is not limited by the particular modes of administration disclosed herein. Standard references in the art (e.g., Remington's Pharmaceutical Sciences, 18th edition, 1990) provide modes of administration and formulations for delivery of various pharmaceutical preparations and formulations in pharmaceutical carriers. Other protocols which are useful for the administration of a therapeutic compound of the invention will be known to one of ordinary skill in the art, in which the dose amount, schedule of administration, sites of administration, mode of administration (e.g., intra-organ) and the like vary from those presented herein.

Administration of a cell or vector to increase a level of a CsChrimson light-activated ion channel or variant thereof, in a mammal other than a human; and administration and use of CsChrimson light-activated ion channels or variants thereof of the invention, e.g. for testing purposes or veterinary therapeutic purposes, is carried out under substantially the same conditions as described above. It will be understood by a skilled artisan that this invention is applicable to both human and animals. Thus, in certain embodiments, this invention is intended to be used in husbandry and veterinary medicine as well as in human therapeutics.

In some aspects of the invention, methods of treatment using a CsChrimson light-activated ion channel or variant thereof of the invention are applied to cells including but not limited to a neuronal cell, a nervous system cell, a neuron, a cardiac cell, a circulatory system cell, a visual system cell, an auditory system cell, a muscle cell, or an endocrine cell, etc.

Disorders, Diseases and Conditions for Treatment with CsChrimson or Variant Thereof Disorders, diseases, and conditions that may be treated using methods of the invention to express CsChrimson or variants thereof in a cell, tissue, and/or subject may include, but are not limited to: injury, brain damage, spinal cord injury, epilepsy, metabolic disorders, cardiac dysfunction, vision loss, blindness, deafness, hearing loss, and neurological conditions (e.g., Parkinson's disease, Alzheimer's disease, seizure), degenerative neurological conditions, etc. In some embodiments of the invention, a disorder, disease, or condition may be treated by expressing a CsChrimson light-activated ion channel or variant thereof in at least one cell and contacting the at least one cell with a wavelength of light suitable to increase ion conductance in the cell. In some embodiments of the invention, such treatments include restoring function in a cell that has a disease or condition, by contacting one or more cells that expresses a CsChrimson light-activated ion channel or variant thereof with a suitable wavelength of light to drive activity patterns in the cell to restore a function in the cell and to ameliorate one or more symptoms of the disorder, disease, or condition.

CsChrimson light-activated ion channels or variants thereof of the invention may be used to target cells and membranes, and to alter voltage-associated cell activities. In some aspects of the invention, a CsChrimson light-activated ion channel or variant thereof of the invention may be used to decrease the pH of a cell in which it is expressed. Such a technique may be used to treat alkalosis in a cell, tissue or subject.

Another aspect of the invention includes methods of using light-activated proton pumps in conjunction with the use of CsChrimson light-activated ion channels or variants thereof of the invention for the coupled effect of hyperpolarization and intracellular alkalinization. For example, both phenomena can induce spontaneous spiking in neurons by triggering hyperpolarization-induced cation currents or pH-dependent hyper-excitability. Another aspect of the invention is to express CsChrimson light-activated ion channels or variants thereof of the invention into cell membranes and then to activate the light-activated ion channels and generate subcellular voltage or pH gradients, particularly at synapses and in synaptic vesicles to alter synaptic transmission, and mitochondria to improve ATP synthesis. In some embodiments of the invention, treatment methods utilizing CsChrimson light-activated ion channels or variants thereof may be used for the treatment of visual system disorders, diseases, conditions, for example to treat vision reduction or loss. A CsChrimson light-activated ion channel of the invention may be administered to a subject who has a vision reduction or loss and the expressed light-activated ion channel can function as light-sensitive cells in the visual system, thereby permitting a gain of visual function in the subject.

The present invention in some aspects, includes one or more of preparing CsChrimson (and CsChrimson variant) nucleic acid sequences and polynucleotide sequences; expressing in cells and membranes polypeptides encoded by the prepared nucleic acid and polynucleotide sequences; illuminating the cells and/or membranes with suitable light, and demonstrating rapid depolarization of the cells and/or a change in conductance across the membrane in response to light, as well as rapid release from depolarization upon cessation of light. The ability to controllably alter voltage across membranes and cell depolarization with light has been demonstrated. The present invention enables light-control of cellular functions in vivo, ex vivo, and in vitro, and the CsChrimson light activated ion channels of the invention and their use, have broad-ranging applications for drug screening, treatments, and research applications, some of which are describe herein.

EXAMPLES

Example 1

A trafficking variant of the Chrimson molecule (described in PCT Publication No. WO2013/071231 and Nature Methods (2014) volume 11(3) 338-346, published online Feb. 9, 2014) was prepared. This trafficking variant, called CsChrimson-KGC-GFP-ER2, is a CsChR-Chrimson chimera, in which the Chrimson N-terminus was replaced with the CsChR N-terminus (see FIG. 1A and FIG. 2). The CsChrimson-KGC-GFP-ER2 construct also included appended KGC and ER2 trafficking sequences (FIG. 1C).

Figure 1B:
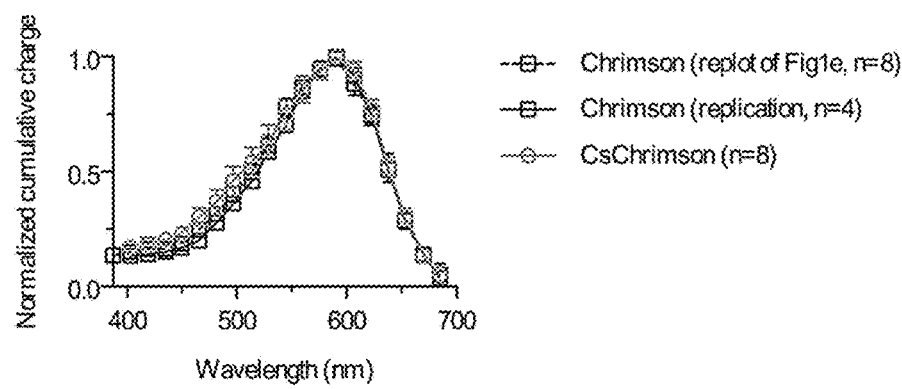
Figure 1C:
Figure 1D:
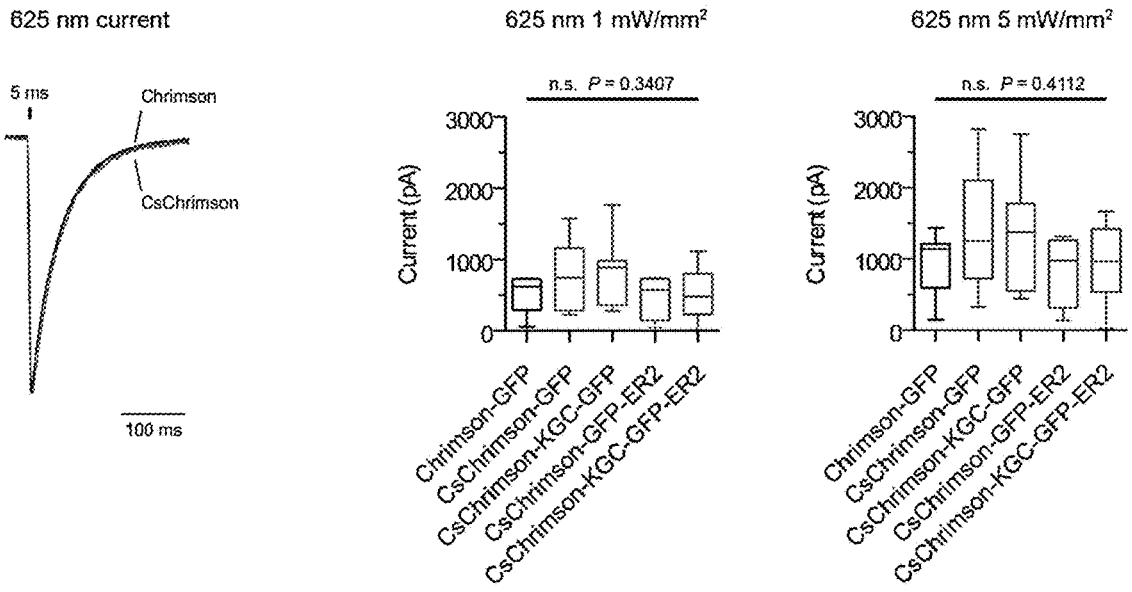
Figure 1E:
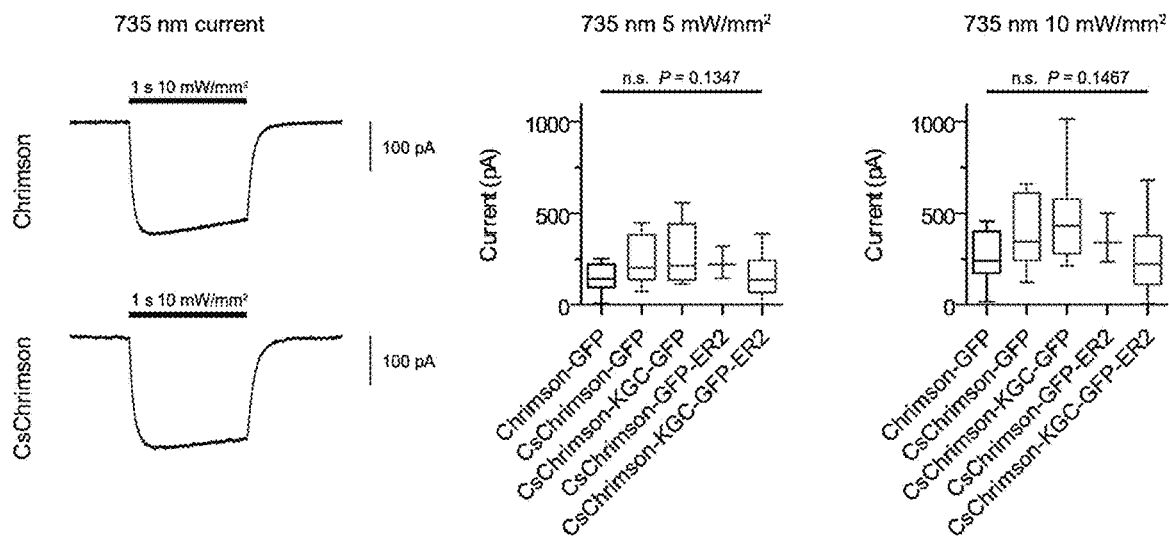
Figure 1F:
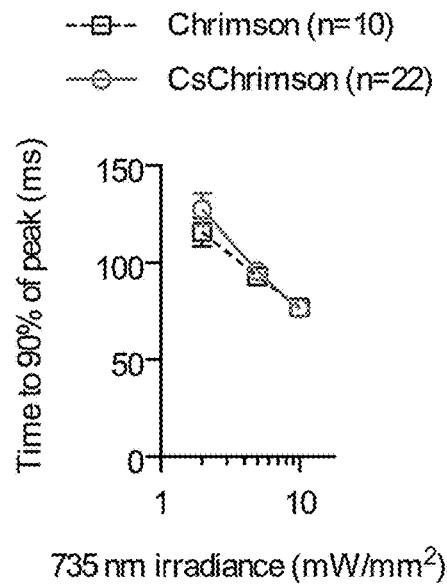
Figure 1G:
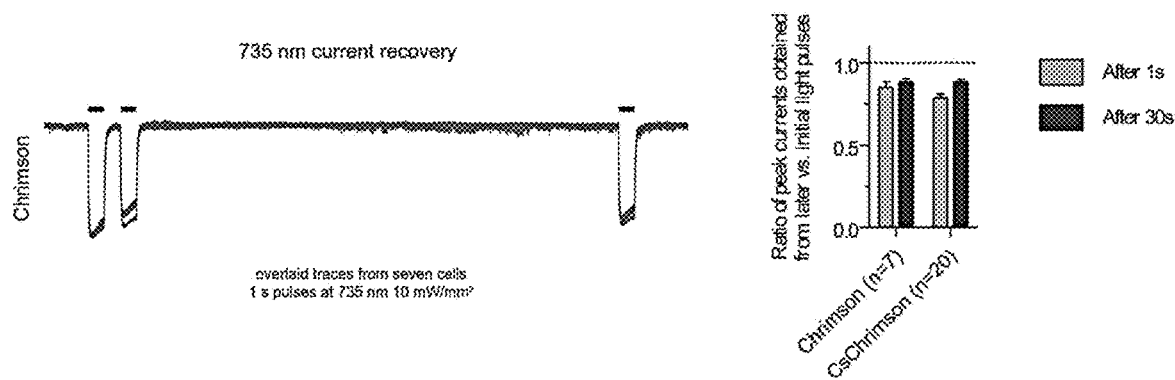
Figure 3:
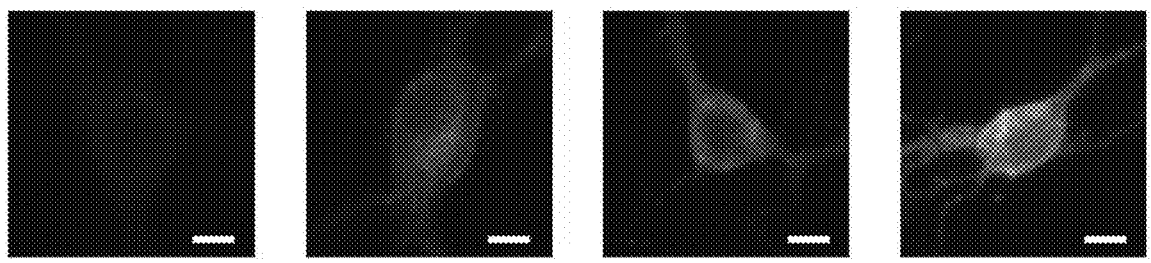
FIG. 3 shows photomicrographic images of trafficking in cultured neurons. The images are of results using various constructs as indicated. Representative GFP epi-fluorescence images for Chrimson and CsChrimson trafficking variants taken on 20× objective and imaged under identical conditions. All images have identical brightness and contrast settings. Scale bar, 10 μm.
Figure 3:
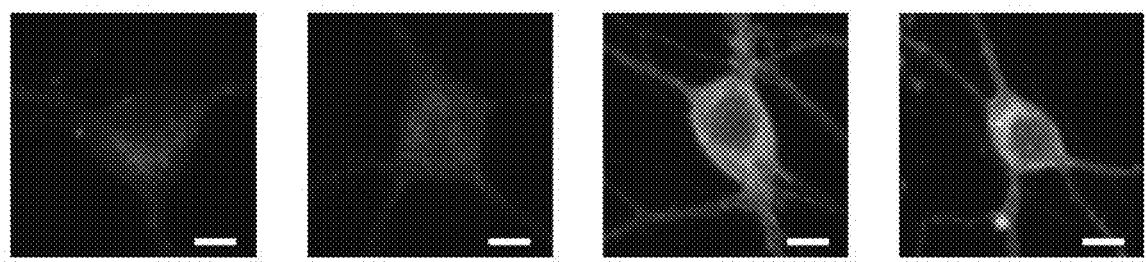
Figure 3:
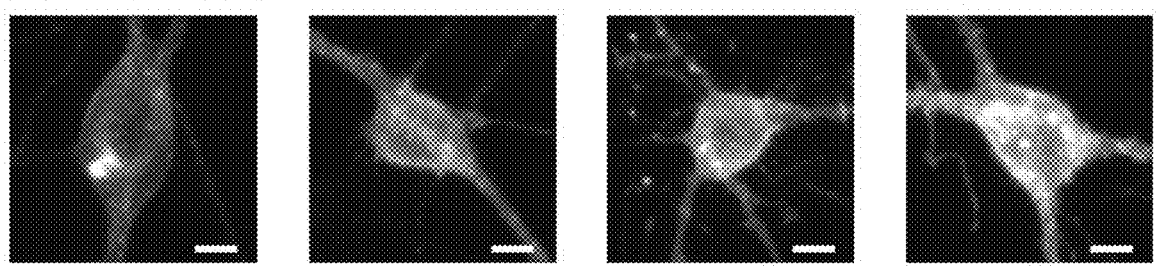
Figure 3:
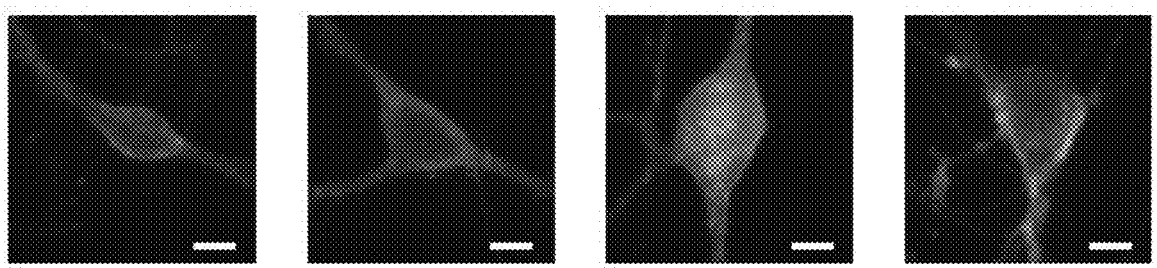
Figure 3:
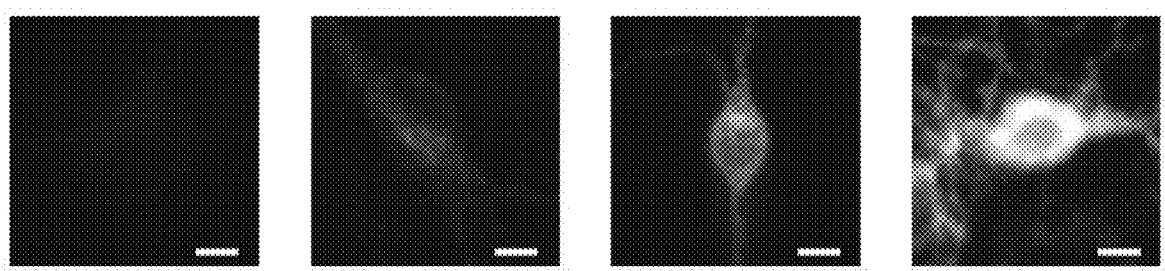

No transmembrane regions were modified, and it was found that expressed CsChrimson had the same spectral and kinetic properties as Chrimson in murine cultured neurons (FIGS. 1B, D, F, and G). In addition, CsChrimson was compared with and without KGC and/or ER2 trafficking sequences and all of the versions were found to have similar photocurrents in cultured neurons as shown in FIGS. 1D and E. However, more cytosolic aggregates were observed with the KGC version and a reduction of aggregates was observed with the ER2 version (see FIG. 3). FIG. 3 provides results showing representative GFP epi-fluorescence images for Chrimson and CsChrimson trafficking variants taken on 20x objective and imaged under identical conditions. All images have identical brightness and contrast settings. Scale bar, 10 µm. It was determined that CsChrimson with the ER2 trafficking sequence can be used in some biological contexts.

Studies were performed to prepare sequences and to express light-activated ion channels in cells, tissues, and subjects. Identifications and amino acid sequences of some of the light-activated ion channels in the examples are ChR88 (SEQ ID NO: 2) and CsChrimson (SEQ ID NO: 1). Non-limiting exemplary methods are set forth Example 1. General methods also applicable to light-activated channel molecules and methods for their use are disclosed in publications such as US Published Application No. 2010/0234273, US Published Application No. 20110165681, Chow B Y, et al. *Methods Enzymol.* 2011; 497: 425-43; Chow, B., et al. *Nature* 2010 Jan. 7; 463(7277): 98-102, and Nature Methods (2014) volume 11(3) 338-346, published online Feb. 9, 2014, the content of each of which is incorporated by reference herein.

Studies were performed to prepare sequences and to express light-activated ion channels in cells, tissues, and subjects. Non-limiting exemplary methods are set forth below.

(a) In Utero Electroporation

All procedures were in accordance with the National Institutes of Health Guide for the Care and Use of Laboratory Animals and approved by the Massachusetts Institute of Technology Committee on Animal Care. C57BL/6J E16-timed pregnant mice were used for electroporation. Surgery was done under ketamine-xylazine anesthesia and buprenorphine analgesia, DNA solution containing plasmids of interest were injected into lateral ventricle of each embryo using a pulled capillary tube. Five square pulses (50 ms width, 1 Hz, 35V) were applied using tweezer electrode for electroporation.

(b) Slice Preparation

P20-P30 mice were used for slice preparation. In younger animals it was difficult to elicit synaptic responses by photostimulating callosal axons. Mice were anesthetized with isofluorane and transcardialy perfused with artificial cerebrospinal fluid (ACSF). The brain was removed and placed in an ice-cold cutting solution containing 110 mM choline chloride, 25 mM $NaHCO_3$, 25 mM D-glucose, 11.6 mM sodium ascorbate, 7 mM $MgCl_2$, 3.1 mM sodium pyruvate, 2.5 mM KCl, 1.25 mM $NaH_2PO_4$ and 0.5 mM $CaCl_2$. 300-mm-thick coronal slices of the visual cortex were cut with a vibrating slicer and incubated in oxygenated ACSF for 45 min at 37° C. before the recordings.

(c) Slice Electrophysiology

Recordings were performed at room temperature (22-24° C.) under constant perfusion of oxygenated ACSF. Neurons were visualized using infrared differential interference optics and patched with borosilicate pipettes (resistance 4-6 MO). The intracellular solution contained 120 mM potassium gluconate, 5 mM NaCl, 2 mM $MgCl_2$, 0.1 mM $CaCl_2$, 10 mM HEPES, 1.1 mM EGTA, 4 mM magnesium ATP, 0.4 mM disodium GTP, (pH 7.25; 290 mOsm). Cells were recorded at a depth of 30-120 um in the brain slice. Photostimulation was done using a blue LED (470 nm; Thorlabs, Newton, NJ) and a red LED (625 nm with 632/22 nm filter; Thorlabs).

(d) Neuron Culture, Transfection, Infection, and Imaging

All procedures involving animals were in accordance with the National Institutes of Health Guide for the care and use of laboratory animals and approved by the Massachusetts Institute of Technology Animal Care and Use Committee. Swiss Webster or C57 mice [Taconic (Hudson, N.Y.) or Jackson Labs (Bar Harbor, ME)] were used. For hippocampal cultures, hippocampal regions of postnatal day 0 or day 1 mice were isolated and digested with trypsin (1 mg/ml) for ~12 min, and then treated with Hanks solution supplemented with 10-20% fetal bovine serum and trypsin inhibitor (Sigma Aldrich, St Louis, Mo.). Tissue was then mechanically dissociated with Pasteur pipettes, and centrifuged at 1000 rpm at 4° C. for 10 min. Dissociated neurons were plated at a density of approximately four hippocampi per 20 glass coverslips, coated with Matrigel (BD Biosciences, San Jose, Calif.). For cortical cultures, dissociated mouse cortical neurons (postnatal day 0 or 1) were prepared as previously described, and plated at a density of 100-200 k per glass coverslip coated with Matrigel (BD Biosciences). Cultures were maintained in Neurobasal Medium supplemented with B27 (Invitrogen [Life Technologies, Grand Isle, NY]) and glutamine. Hippocampal and cortical cultures were used interchangeably; no differences in reagent performance were noted.

Neurons were transfected at 3-5 days in vitro using calcium phosphate (Invitrogen). GFP fluorescence was used to identify successfully transfected neurons. Alternatively, neurons were infected with 0.1-3 µl of lentivirus or adeno-associated virus (AAV) per well at 3-5 days in vitro.

(e) HEK 293FT Cell Culture and Transfection

HEK 293FT cells (Invitrogen) were maintained between 10-70% confluence in D10 medium (Cellgro [Mediatech/Corning, Manassas, Va.]) supplemented with 10% fetal bovine serum (Invitrogen), 1% penicillin/streptomycin (Cellgro), and 1% sodium pyruvate (Biowhittaker, Walkersville, MD). For recording, cells were plated at 5-20% confluence on glass coverslips coated with Matrigel (BD Biosciences). Adherent cells were transfected approximately 24 hours post-plating either with TransLT 293 lipofectamine transfection kits (Mirus Bio, LLC, Madison, Wis.) or with calcium phosphate transfection kits (Invitrogen), and recorded via whole-cell patch clamp between 36-72 hours post-transfection.

(f) In Vitro Whole Cell Patch Clamp Recording & Optical Stimulation

Whole cell patch clamp recordings were made using a Multiclamp 700B amplifier, a Digidata 1440 digitizer, and a PC running pClamp (Molecular Devices). Neurons were bathed in room temperature Tyrode containing 125 mM NaCl, 2 mM KCl, 3 mM $CaCl_2$, 1 mM $MgCl_2$, 10 mM HEPES, 30 mM glucose, 0.01 mM NBQX and 0.01 mM GABAzine. The Tyrode pH was adjusted to 7.3 with NaOH and the osmolarity was adjusted to 300 mOsm with sucrose. HEK cells were bathed in a Tyrode bath solution identical to that for neurons, but lacking GABAzine and NBQX. Borosilicate glass pipettes (Warner Instruments, Hamden, CT) with an outer diameter of 1.2 mm and a wall thickness of 0.255 mm were pulled to a resistance of 3-9 MΩ with a P-97 Flaming/Brown micropipette puller (Sutter Instruments, Novato, Calif.) and filled with a solution containing 125 mM K-gluconate, 8 mM NaCl, 0.1 mM $CaCl_2$, 0.6 mM $MgCl_2$, 1 mM EGTA, 10 mM HEPES, 4 mM Mg-ATP, and 0.4 mM Na-GTP. The pipette solution pH was adjusted to 7.3 with KOH and the osmolarity was adjusted to 298 mOsm with sucrose. Access resistance was 5-30 MΩ, monitored throughout the voltage-clamp recording. Resting membrane potential was ~−60 mV for neurons and ~−30 mV for HEK 293FT cells in current-clamp recording.

Photocurrents were measured with 500 ms light pulses in neurons voltage-clamped at −60 mV, and in HEK 293FT cells voltage-clamped at −30 mV. Light-induced membrane hyperpolarizations were measured with 500 ms light pulses in cells current-clamped at their resting membrane potential. Light pulses for all wavelengths except 660 nm and action spectrum characterization experiments were delivered with a DG-4 optical switch with 300 W xenon lamp (Sutter Instruments), controlled via TTL pulses generated through a Digidata signal generator. Green light was delivered with a 575±25 nm bandpass filter (Chroma) and a 575±7.5 nm bandpass filter (Chroma Technology Group, Bellows Falls, VT). Action spectra were taken with a Till Photonics Polychrome V, 150 W Xenon lamp, 15 nm monochromator bandwidth.

Data was analyzed using Clampfit (Molecular Devices) and MATLAB (Mathworks, Inc.)

(g) Ion Conductance Recording

Whole-cell patch clamp recordings were performed in isolated HEK293FT cells to accurately measure parameters from single cells. All recordings were performed using an Axopatch 200B amplifier and Digidata 1440 digitizer (Molecular Devices) at room temperature. In order to allow isolated cell recording, cells were plated at a lower density of 15,000 cells per well in 24-well plates that contained round glass coverslips (0.15 mm thick, 25 mm in diameter, coated with 2% Growth Factor Reduced Matrigel in DMEM for 1 h at 37° C.). For most recordings, Tyrode was used as the extracellular solution, and the intracellular solution consisted of (in mM) 125 K-Gluconate, 8 NaCl, 0.1 $CaCl_2$, 0.6 $MgCl_2$, 1 EGTA, 10 HEPES, 4 MgATP, 0.4 NaGTP, pH 7.3 (KOH adjusted), with 295-300 mOsm (sucrose adjusted). Extracellular and intracellular solutions used for testing ion permeability are listed in Table 1.

TABLE 1

Compositions of solutions used in ion permeability experiments

| Solution | [Na] (mM) | [K] (mM) | [Ca] (mM) | [H] (mM) | pH | Other |
|---|---|---|---|---|---|---|
| Intracellular | 0 | 140 | 0 | 5.10E−05 | 7.4 | 5 mM EGTA, 2 mM MgCl2, 10 mM HEPES |
| 145 mM NaCl | 145 | 5 | 1 | 5.10E−05 | 7.4 | 10 mM HEPES, 5 mM glucose, 2 mM MgCl2 |
| 145 mM KCl | 0 | 145 | 1 | 5.10E−05 | 7.4 | 10 mM HEPES, 5 mM glucose, 2 mM MgCl2 |
| 90 mM CaCl2 | 0 | 5 | 91 | 5.10E−05 | 7.4 | 10 mM HEPES, 5 mM glucose, 2 mM MgCl2 |
| 5 mM NaCl | 5 | 5 | 1 | 5.10E−04 | 6.4 | 135 mM NMDG, 10 mM HEPES, 5 mM glucose, 2 mM MgCl2 |

Liquid junction potentials were measured using standard procedures to be 5.8 mV for the 90 mM $CaCl_2$ and 4.9 mV for the 5 mM NaCl extracellular solutions, which were corrected during recording; the others were <1 mV in junction potential.

In all patch clamp recordings, a stringent cutoff of access resistance less than 25 MΩ and holding current less than ±50 pA was applied in order to ensure accurate measurement. Typical membrane resistance was between 500 MΩ-2 GΩ and pipette resistance was between 4-10 MΩ.

Photostimulation of patch clamped cells was conducted by a 470 nm LED (Thorlabs) at 10 mW/mm$^2$ unless otherwise stated. For most experiments, 1 s illumination was delivered to measure transient and steady-state photocurrents.

(h) Plasmid Construction and Site Directed Mutagenesis

Opsins were mammalian codon-optimized, and synthesized by Genscript (Genscript Corp., NJ). Opsins were fused in frame, without stop codons, ahead of GFP (using BamHI and AgeI) in a lentiviral vector containing the CaMKII promoter, enabling direct neuron transfection, HEK cell transfection (expression in HEK cells is enabled by a ubiquitous promoter upstream of the lentiviral cassette), and lentivirus production and transfection. Amino acid sequences of some opsins that were tested were as follows: ChR88 (SEQ ID NO: 2) and CsChrimson (SEQ ID NO: 1).

The 'ss' signal sequence from truncated MHC class I antigen corresponded to amino acid sequence (M)VPCTLLLLLAAALAPTQTRA (SEQ ID NO: 8), DNA sequence gtcccgtgcacgctgctcctgctgttggcagccgccctggctccgactcagacgcgggcc (SEQ ID NO: 7). The 'ER2' ER export sequence corresponded to amino acid sequence FCYENEV (SEQ ID NO: 10), DNA sequence ttctgctacgagaatgaagtg (SEQ ID NO: 9). The 'KGC' signal sequence corresponded to amino acid sequence KSRITSEGEYIPLDQIDINV (SEQ ID NO: 12), DNA sequence of KGC signal sequence:

aaatccagaattacttctgaagggggagtatatccctctggatcaaatagacat-
caatgtt. (SEQ ID NO: 11).

Point mutants for HEK cell testing were generated using the QuikChange kit [Stratagene, (Agilent Technologies, Santa Clara, Calif.)] on the opsin-GFP fusion gene inserted between BamHI and AgeI sites in a modified version of the pEGFP-N3 backbone [Invitrogen, (Life Technologies Corporation, Carlsbad, Calif.)]. All constructs were verified by sequencing.

(i) Lentivirus Preparation

HEK293FT cells [Invitrogen, (Life Technologies Corporation, Carlsbad, Calif.)] were transfected with the lentiviral plasmid, the viral helper plasmid pΔ8.74, and the pseudotyping plasmid pMD2.G. The supernatant of transfected HEK cells containing virus was then collected 48 hours after transfection, purified, and then pelleted through ultracentrifugation. Lentivirus pellet was resuspended in phosphate buffered saline (PBS) and stored at −80° C. until further usage in vitro or in vivo. The estimated final titer is approximately $10^9$ infectious units/mL.

Example 2

Whole-cell patch clamp recordings were made using a Multiclamp 700B amplifier and a Digidata 1550 digitizer (Molecular Devices, Sunnyvale, Calif.). Additional experimental conditions are the same as previously described in PCT Publication No. WO2013/071231. Light-activated ion channels ChR88 and CsChrimson were expressed in cultured hippocampal neurons using neuron culture, transfection, infection, and imaging methods described in Example 1. In vitro whole cell patch claim recording and optical stimulation were conducted on the neurons using methods described in Example 1. In addition, *Drosophila* experiments using methods described in Nature Methods (2014) volume 11(3) 338-346, published online Feb. 9, 2014 for the trafficking variant of the Chrimson molecule were also performed using the CsChrimson trafficking construct.

Results of experiments to characterize CsChrimson and CsChrimson constructs used to express CsChrimson are shown in FIG. 1. FIG. 1A provides a schematic of a CsChrimson chimera, which illustrates that the CsChR section is at the N-terminal non-transmembrane region and the Chrimson sequence includes the transmembrane regions. FIG. 1C shows a schematic of trafficking sequences used to generate the CsChrimson *Drosophila* transgenics. FIGS. 1D and 1E show maximum photocurrents in response to contact by red (625-nm) and far-red (735-nm) light as measured in cultured neurons. FIGS. 1F and 1G show "Turn-on" kinetics (FIG. 1F) and "recovery" kinetics (FIG. 1G) in response to contact with 735-nm light. The CsChrimson kinetic data were pooled from all trafficking versions. All constructs in this panel were expressed under CaMKII promoter and selected based solely on the presence of co-transfected cytosolic tdTomato expression. Illumination conditions were as labeled in each panel. Box plot whiskers represent minimum and maximum data points. Box limits represent $25^{th}$ percentile, median, and $75^{th}$ percentile. Statistics: n=7 to 12 cells for all constructs except for CsChrimson-GFP-ER2, which has n=4 cells in FIG. 1D and n=3 cells in FIG. 1E. Plotted data are mean±s.e.m. in FIGS. 1B, 1F, and 1G. ANOVA with Dunnett's post hoc test with Chrimson-GFP as reference in FIGS. 1D and 1E.

Figure 2:
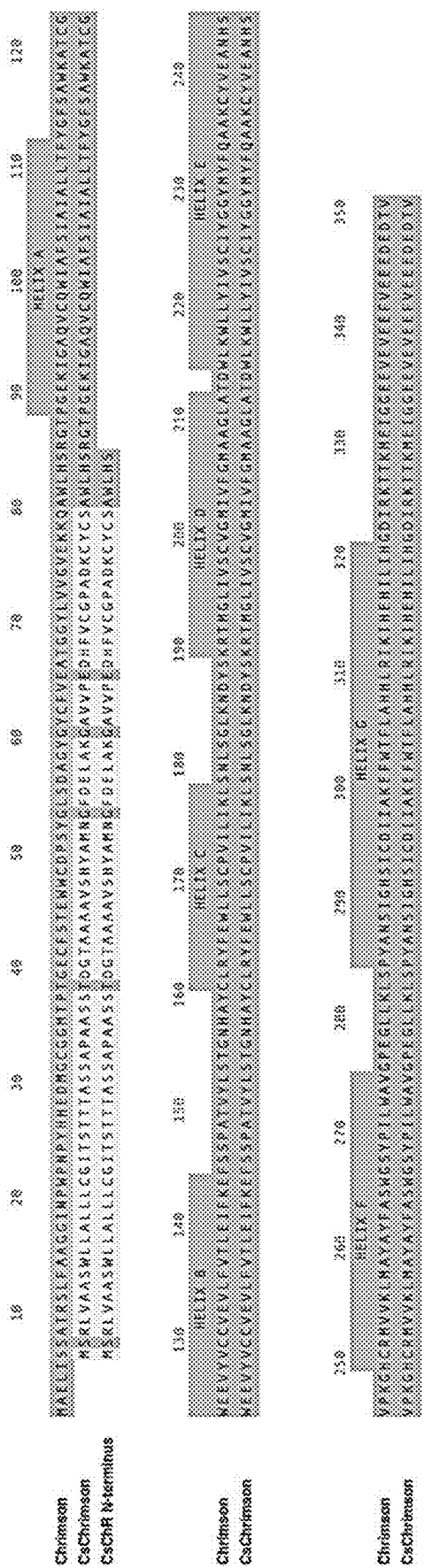
FIG. 2 shows the amino acid sequence of CsChrimson (SEQ ID NO: 1). The transmembrane regions are based on an alignment against C1C2 crystal structure. The amino acid sequence of Chrimson (SEQ ID NO: 2) and the amino acid sequence of an CsChR N-terminal fragment (SEQ ID NO: 6) are also shown in alignment with CsChrimson. Putative transmembrane helices are flagged. The regions of the aligned sequences from the start to approximately nucleotide 80 in the alignment illustrate differences between Chrimson and CsChrimson sequences.

FIG. 2 provides the CsChrimson polypeptide sequence (SEQ ID NO: 1) and shows alignment with the Chrimson polypeptide (SEQ ID NO: 2) and CsChR N-terminus polypeptide (SEQ ID NO: 6) sequences. FIG. 2 shows that the CsChrimson polypeptide is a chimera that includes a portion of the amino acid sequence of Chrimson and an N-terminal portion of CsChR. SEQ ID NO: 6 is an N-terminal portion of the CsChR polypeptide, which is set forth herein as SEQ ID NO: 5. The transmembrane regions were based on an alignment against C1C2 crystal structure. Putative transmembrane helices are shown. The alignment shows the amino acid differences between the Chrimson and CsChrimson sequences.

Example 3

Action Spectrum Studies

HEK 293FT cells were transfected to express Chrimson and CsChrimson light-activated ion channels using methods of Example 1. In vitro whole cell patch claim recording and optical stimulation were conducted on the transfected, cultured cells using methods described in Example 1. FIG. 1B shows an action spectra for Chrimson and CsChrimson, as well as the Chrimson spectrum data previously obtained (see Nature Methods (2014) volume 11(3) 338-346, published online Feb. 9, 2014). The experiments were performed using HEK293 cells; measured using equal photon fluxes of $~2.5 \times 10^{21}$ photons/s/m$^2$). Both Chrimson and CsChrimson were red-light sensitive.

Example 4

CsChrimson and Chrimson genes were expressed in cells using methods provided below.

Genes

The opsin gene encoding the CsChrimson polypeptide set forth herein as SEQ ID NO: 1 and the opsin gene encoding the Chrimson polypeptide set forth herein as SEQ ID NO: 2 are expressed in cells as follows.

Methods (1) The opsin gene was cloned into a lentiviral or adeno-associated virus (AAV) packaging plasmid, or another desired expression plasmid, and then clone GFP downstream of the preferred gene, eliminating the stop codon of the opsin gene, thus creating a fusion protein.

(2) The viral or expression plasmid contained either a strong general promoter, a cell-specific promoter, or a strong general promoter followed by one more logical elements (such as a lox-stop-lox sequence, which will be removed by Cre recombinase selectively expressed in cells in a transgenic animal, or in a second virus, thus enabling the strong general promoter to then drive the gene.

(3) If using a viral plasmid, synthesize the viral vector using the viral plasmid.

(4) If using a virus, as appropriate for gene therapy (over 600 people have been treated with AAV carrying various genetic payloads to date, in 48 separate clinical trials, without a single adverse event), inject the virus using a small needle or cannula into the area of interest, thus delivering the gene encoding the opsin fusion protein into the cells of interest. If using another expression vector, directly electroporate or inject that vector into the cell or organism (for acutely expressing the opsin, or making a cell line, or a transgenic mouse or other animal).

(5) Illuminate with light. For Chrimson and CsChrimson, peak illumination wavelengths are 590 nm+/−15 nm, and experiments are also performed using illumination wavelengths of 625 nm and 735 nm.

6) To illuminate two different populations of cells (e.g., in a single tissue) with two different colors of light, first target one population with CsChrimson, and the other population with a light-activated ion channel (for example, Chronos as previously described in Nature Methods (2014) volume 11(3) 338-346, published online Feb. 9, 2014), using two different viruses (e.g., with different coat proteins or promoters) or two different plasmids (e.g., with two different promoters). Then, after the molecule expresses, illuminate the tissue with 470±10 nm or 406±10 nm light to preferentially depolarize the Chronos-expressing cells, and illuminate the tissue with 406±10 nm or 660±10 nm light, to preferentially depolarize the CsChrimson-expressing cells. (7) The above wavelengths illustrate typical modes of operation, but are not meant to constrain the protocols that can be used. Either narrower or broader wavelengths, or differently-centered illumination spectra, can be used. For prosthetic uses, the devices used to deliver light may be implanted. For drug screening, a xenon lamp or LED can be used to deliver the light.

Aspects of the invention include compositions of matter that have been reduced to practice, as described below:

Plasmids encoding for the above genes, have been prepared and used to deliver genes into cells, where the genes have been expressed. As an exemplary vector, lentiviruses carrying payloads encoding for the above genes have been prepared and used to deliver genes into cells resulting in expression of the light activated ion channels in the cells. In addition, adeno-associated viruses carrying payloads encoding for the above genes have been prepared and used to deliver genes into cells, resulting in the expression of the light activated ion channels in the cells. Cells have been prepared that express the light activated ion channels genes set forth in Example 2. *Drosophila* CsChrimson transgenic organisms have been prepared. The drosophila transgenics were prepared using a CsChrimson-KGC-mVenus-ER2 construct via standard methods. Thus, organisms have been prepared that include cells that express the light activated ion channels genes disclosed herein.

Example 5

Two-color assays are performed. Chronos (for blue light activation) and CsChrimson (for red light activation) are expressed in separate sets cells that represent non-overlapping neuronal populations. Following expression, the cell population is exposed to light and the wavelength and timing and "dose" of light is optimized using the following parameters.

The population is contacted with blue light having a wavelength between 450 nm to 500 nm, and with a pulse width of between 1 and 5 ms for activation. A pulse width of 5 ms provides for minimum sub-threshold crosstalk in the blue light, which is defined as <15 mV, <10 mV, and optimally as <5 mV.

(1) The maximum blue light power that can be used is determined using by patch clamping CsChrimson expressing cells, illuminating with blue light and measuring voltage deflection. Optimally using blue light power such that maximum voltage deflection is <10 mV, usually 0.4 to 0.6 mW/mm$^2$.

(2) The optimal blue light power that can be used to drive Chronos is determined using the same conditions as above in (1), except using lower light power, such as 50 $\mu$W/mm$^2$ to 0.4 mW/mm$^2$, and optimally 0.2 mW/mm$^2$. Power depends on expression system and cell type used in the study.

The population is contacted with red light having a wavelength between 620 nm to 640 nm, and with a pulse width of between 1 and 5 ms for activation, which may be optimized at 5 ms. The optimal light power to drive CsChrimson in the red is determined by ramping light powers from 0.5 mW/mm$^2$ to 10 mW/mm$^2$. The method is optimized such that a minimum red light power is used to achieve 100% spiking for CsChrimson.

EQUIVALENTS

It is to be understood that the methods and compositions that have been described above are merely illustrative applications of the principles of the invention. Numerous modifications may be made by those skilled in the art without departing from the scope of the invention.

Although the invention has been described in detail for the purpose of illustration, it is understood that such detail is solely for that purpose and variations can be made by those skilled in the art without departing from the spirit and scope of the invention which is defined by the following claims.

The contents of all literature references, publications, patents, and published patent applications cited throughout this application are incorporated herein by reference in their entirety.

The invention claimed is:

1. A CsChrimson light-activated ion channel polypeptide comprising (a) the amino acid sequence set forth as SEQ ID NO: 1 or (b) the amino acid sequence of SEQ ID NO: 1 with one, two, three, or more amino acid sequence modifications within the sequence, and having at least 97% identity to amino acids 1-79 of SEQ ID NO: 1 and a seven-transmembrane-domain region having at least 97% identity to amino acids 80-315 of SEQ ID NO: 1, wherein the CsChrimson light-activated ion channel polypeptide is capable of being activated with light, and the activation alters ion conductivity of the CsChrimson light-activated ion channel polypeptide.

2. A membrane comprising the CsChrimson light-activated ion channel polypeptide of claim 1.

3. The membrane of claim 2, wherein the membrane is a mammalian cell membrane.

4. The membrane of claim 3, wherein the membrane is a cell membrane of a neuronal cell, a nervous system cell, a cardiac cell, a circulatory system cell, a visual system cell, or an auditory system cell.

5. A cell comprising the CsChrimson light-activated ion channel polypeptide of claim 1.

6. The cell of claim 5, wherein the cell is an excitable cell.

7. The cell of claim 6, wherein activating the CsChrimson light-activated ion channel polypeptide depolarizes the cell.

8. The cell of claim 5, wherein the cell is in a subject.

9. The CsChrimson light-activated ion channel polypeptide of claim 1, having at least 97% identity to amino acids 1-79 of SEQ ID NO: 1 and a seven-transmembrane-domain region having 98% identity to amino acids 80-315 of SEQ ID NO: 1.

10. The CsChrimson light-activated ion channel polypeptide of claim 1, having at least 97% identity to amino acids 1-79 of SEQ ID NO: 1 and a seven-transmembrane-domain region having 99% identity to amino acids 80-315 of SEQ ID NO: 1.

11. The CsChrimson light-activated ion channel polypeptide of claim 1, having at least 98% identity to amino acids 1-79 of SEQ ID NO: 1 and a seven-transmembrane-domain region having 97% identity to amino acids 80-315 of SEQ ID NO: 1.

12. The CsChrimson light-activated ion channel polypeptide of claim 1, having at least 98% identity to amino acids 1-79 of SEQ ID NO: 1 and a seven-transmembrane-domain region having 98% identity to amino acids 80-315 of SEQ ID NO: 1.

13. The CsChrimson light-activated ion channel polypeptide of claim 1, having at least 98% identity to amino acids 1-79 of SEQ ID NO: 1 and a seven-transmembrane-domain region having 99% identity to amino acids 80-315 of SEQ ID NO: 1.

14. The CsChrimson light-activated ion channel polypeptide of claim 1, having at least 98% identity to amino acids 1-79 of SEQ ID NO: 1 and a seven-transmembrane-domain region having 100% identity to amino acids 80-315 of SEQ ID NO: 1.

15. The CsChrimson light-activated ion channel polypeptide of claim 1, having at least 100% identity to amino acids 1-79 of SEQ ID NO: 1 and a seven-transmembrane-domain region having 97% identity to amino acids 80-315 of SEQ ID NO: 1.

16. The CsChrimson light-activated ion channel polypeptide of claim 1, having at least 100% identity to amino acids 1-79 of SEQ ID NO: 1 and a seven-transmembrane-domain region having 98% identity to amino acids 80-315 of SEQ ID NO: 1.

17. The CsChrimson light-activated ion channel polypeptide of claim 1, having at least 100% identity to amino acids 1-79 of SEQ ID NO: 1 and a seven-transmembrane-domain region having 99% identity to amino acids 80-315 of SEQ ID NO: 1.

18. A method of altering ion conductivity of a membrane, the method comprising,
   a) expressing in a host membrane a CsChrimson light-activated ion channel polypeptide comprising (a) the amino acid sequence set forth as SEQ ID NO: 1 or (b) the amino acid sequence of SEQ ID NO: 1 with one, two, three, or more amino acid sequence modifications within the sequence, and having at least 97% identity to amino acids 1-79 of SEQ ID NO: 1 and a seven-transmembrane-domain region having at least 97% identity to amino acids 80-315 of SEQ ID NO: 1, and wherein the CsChrimson light-activated ion channel polypeptide is capable of being activated with light, and the activation alters ion conductivity of the CsChrimson light-activated ion channel polypeptide; and
   b) contacting the CsChrimson light-activated ion channel polypeptide with a light under suitable conditions to activate the light-activated ion channel and alter the ion conductivity of the membrane.

19. The method of claim 18, wherein the host membrane is a cell membrane.

20. The method of claim 18, wherein the membrane is a cell membrane of a neuronal cell, a nervous system cell, a cardiac cell, a circulatory system cell, a visual system cell, or an auditory system cell.

21. The method of claim 18, wherein the CsChrimson light-activated ion channel polypeptide has at least 97% identity to amino acids 1-79 of SEQ ID NO: 1 and 98% identity to amino acids 80-315 of SEQ ID NO: 1.

22. The method of claim 18, wherein the host membrane is in a cell.

23. The method of claim 22, wherein the cell is a human cell.

24. The method of claim 22, wherein altering the ion conductivity of the membrane depolarizes the cell.

25. A method of assessing the effect of a candidate compound on ion conductivity of a membrane, the method comprising,
  a) contacting a test membrane comprising a light-activated ion channel polypeptide comprising (a) the amino acid sequence set forth as SEQ ID NO: 1 or (b) the amino acid sequence of SEQ ID NO: 1 with one, two, three, or more amino acid sequence modifications within the sequence, and having at least 97% identity to amino acids 1-79 of SEQ ID NO: 1 and a seven-transmembrane-domain region having at least 97% identity to amino acids 80-315 of SEQ ID NO: 1, and wherein the CsChrimson light-activated ion channel polypeptide is capable of being activated with light, and the activation alters ion conductivity of the CsChrimson light-activated ion channel polypeptide, with light under conditions suitable for altering ion conductivity of the test membrane;
  b) contacting the test membrane with a candidate compound; and
  c) identifying the presence or absence of a change in ion conductivity of the test membrane contacted with the light and the candidate compound compared to ion conductivity of with "a control test membrane comprising the light-activated ion channel polypeptide contacted with light, and not contacted with the candidate compound;
wherein a change in the ion conductivity of the test membrane compared to the control indicates an effect of the candidate compound on the ion conductivity of the test membrane.

26. The method of claim 25, wherein the CsChrimson light-activated ion channel polypeptide has at least 97% identity to amino acids 1-79 of SEQ ID NO: 1 and 98% identity to amino acids 80-315 of SEQ ID NO: 1.

27. The method of claim 25, wherein the membrane is in a cell.

28. The method of claim 27, wherein altering the ion conductivity of the membrane depolarizes the cell.

* * * * *